United States Patent
Buck et al.

(10) Patent No.: US 8,231,562 B2
(45) Date of Patent: Jul. 31, 2012

(54) INSULIN PUMP CONFIGURATION PROGRAMMING INVALID SETTINGS NOTIFICATION AND CORRECTION

(75) Inventors: Schuyler Buck, Muncie, IN (US); Jason Bush, Fishers, IN (US); Kristin Davenport, Fortville, IN (US); David Bradley Markisohn, Indianapolis, IN (US); Leon R. Organ, III, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 737 days.

(21) Appl. No.: 12/205,587

(22) Filed: Sep. 5, 2008

(65) Prior Publication Data

US 2010/0064257 A1 Mar. 11, 2010

(51) Int. Cl.
G06F 3/048 (2006.01)
G06F 9/44 (2006.01)
(52) U.S. Cl. .......... 604/9; 604/892.1; 715/838; 715/772
(58) Field of Classification Search .................. 715/838, 715/771, 772
See application file for complete search history.

(56) References Cited

U.S. PATENT DOCUMENTS

| | | | |
|---|---|---|---|
| 6,341,359 B1 * | 1/2002 | Aiken et al. .................. 714/100 |
| 6,690,972 B2 * | 2/2004 | Conley et al. .................. 607/31 |
| 2003/0163223 A1 * | 8/2003 | Blomquist .................... 700/282 |
| 2003/0163789 A1 * | 8/2003 | Blomquist .................... 715/526 |
| 2005/0097238 A1 * | 5/2005 | Oomori et al. ................. 710/15 |
| 2005/0277911 A1 * | 12/2005 | Stewart et al. ............. 604/890.1 |
| 2006/0129932 A1 * | 6/2006 | Weber et al. .................. 715/705 |
| 2007/0016449 A1 | 1/2007 | Cohen et al. |
| 2007/0033074 A1 | 2/2007 | Nitzan et al. |
| 2007/0066956 A1 | 3/2007 | Finkel |
| 2007/0106135 A1 | 5/2007 | Sloan et al. |
| 2007/0112298 A1 | 5/2007 | Mueller, Jr. et al. |
| 2007/0118405 A1 * | 5/2007 | Campbell et al. ................. 705/2 |
| 2007/0244897 A1 * | 10/2007 | Voskuil et al. .................... 707/9 |
| 2007/0258083 A1 * | 11/2007 | Heppell et al. .................. 356/39 |
| 2008/0059898 A1 * | 3/2008 | Deggelmann et al. ........ 715/764 |
| 2008/0287922 A1 * | 11/2008 | Panduro .................... 604/890.1 |
| 2009/0150176 A1 * | 6/2009 | Gejdos et al. .................... 705/2 |
| 2009/0164239 A1 * | 6/2009 | Hayter et al. .................... 705/2 |
| 2009/0164251 A1 * | 6/2009 | Hayter .............................. 705/3 |

OTHER PUBLICATIONS

Disetronic, "DiagLog Pump Programming Tool," Reference Manual, ver. 02 (Jun. 2005).
Medtronic Minimed, "Solutions Pumps and Meters Software," Manual, ver7.0 (2005).
Disetronic Medical Systems AG, "Accu-Chek Insulin Pump Configuration Software," User Manual, (2005).
Animans Corporation, "ezManager PLUS," User Manual, (2007).

* cited by examiner

*Primary Examiner* — Boris Pesin
*Assistant Examiner* — Daeho Song
(74) *Attorney, Agent, or Firm* — Faegre Baker Daniels LLP

(57) ABSTRACT

An insulin pump configuration programming approach is disclosed that permits setting parameters of pump configuration files to invalid values. An operator may continue with the programming workflow after setting the invalid value. The configuration file including the invalid value may be saved to a memory location of a computing device, but cannot be saved to the pump. Invalid item icons are presented when a parameter is set to an invalid value, and instructions for correcting the invalidity condition are provided when an invalid item icon is hovered over using a pointing device.

20 Claims, 25 Drawing Sheets

INSULIN PUMP CONFIGURATION PROGRAMMING INVALID SETTINGS NOTIFICATION AND CORRECTION

FIELD OF THE INVENTION

The present teachings generally relate to programming insulin pumps and more specifically to pump configuration software that permits operators to set pump parameters to invalid settings.

BACKGROUND

An insulin pump is a fluid infusion device for delivering insulin to people who suffer from diabetes. The pump, which is worn by the user and eliminates the need for multiple daily insulin injections, closely imitates a normally functioning pancreas by releasing hundreds of small doses of insulin each day into the body through an infusion set to regulate blood glucose levels. The rate of delivery of these small doses (i.e., the basal rate) varies from user to user. Indeed, even for a particular user, the basal rate varies throughout the day, and depends upon a variety of factors such as the user's internal clock, metabolism, physical health, and level of stress and exercise.

A basal rate profile consists of one or more basal rates defined to cover the 24 hours of the day (e.g., 24 hourly basal rates). Although portions of this description refer to hourly basal rates and hourly basal rate profiles, it should be understood that basal rates may cover more or less than a one hour time period. Indeed, the time periods covered by basal rates in a profile need not be equal. The concepts of the present disclosure are not limited by the duration of an individual basal rate, and the references to hourly basal rates are only exemplary. Many users use different basal rate profiles for different circumstances. For example, one basal rate profile may be used for weekdays, another profile (i.e., with different hourly basal rates) for weekends, and another profile for vacation days. These different basal rate profiles are designed to accommodate the expected differences in the user's background insulin needs resulting from variations in the user's sleep patterns, levels of exercise and stress, health condition, menstrual cycle status, etc. during such periods. Pumps also deliver (either automatically or when activated by the user) bolus doses of insulin (in addition to the basal rate) before meals or snacks to compensate for caloric intake.

As the amount and rate of insulin delivery (both basal and bolus) must be tailored to the individual needs of the user, modern pumps are programmable. Some pumps are capable of communicating with a separate computing device, and are compatible with software applications that may be executed on the computing device. The software permits an operator, such as the user or a health care provider, to customize the settings of the various parameters that affect the pump's operation. These parameters are included in a configuration file that is executed by the pump, and include hourly basal rates, maximum hourly basal rates, bolus dose settings, communication settings, battery settings, and many others. For example, using programming software, a user may upload the configuration file from the user's pump, modify the settings for certain parameters to change the operation of the pump, and save the modified configuration file to the pump. Alternatively, a health care provider responsible for programming the pumps of multiple patients may select an initial configuration file stored on a pump or computing device as a starting point for programming the patients' pumps. Many of the parameter settings of the initial configuration file (e.g., battery type, language, etc.) may be suitable for all of the pumps to be programmed. Other settings (e.g., hourly basal rates, bolus dose settings, etc.) may be unique to each patient's pump. After the health care provider selects the initial configuration file, he or she may change only the settings needed to customize the pump's operation for the current patient, then save the customized configuration file to the patient's pump without having to define a setting for every pump parameter.

As suggested by the foregoing, insulin pumps perform relatively complex functions, which directly affect the health of the user. For at least these reasons, programming software is generally designed to simplify, to the extent possible, the processes for programming pump functions while simultaneously incorporating safety measures to prevent operators from inadvertently programming a pump with parameter settings that may harm the user. One safety measure incorporated by some programming software applications is a workflow structure that prevents operators from selecting invalid settings for pump parameters. Many pump parameters are dependent upon one another. For example, the range of settings available for an hourly basal rate depends upon the setting of the maximum hourly basal rate parameter. Thus, conventional programming software may prevent the operator from selecting an hourly basal rate that exceeds the current maximum hourly basal rate parameter. If the operator must set an hourly basal rate value in excess of the current maximum, the operator must first set the hourly basal rate to an undesired value, change the current maximum value, then re-set the hourly basal rate to the desired, higher value. In this manner, conventional software imposes sequential workflows designed to prevent operators from making changes to parameters that would, if permitted, violate a relationship with one or more previously defined parameters.

Although it is desirable to reduce the possibility of programming a pump with an invalid parameter setting, it is also desirable to provide flexibility to the operator. In some situations, the operator may wish to set a parameter to an invalid value and take the time to correct the invalidity condition later when it is more convenient. As long as the risk of programming a pump with an invalid parameter setting is managed by the software, permitting the operator to set parameters in the sequence of the operator's choosing (even though some settings may be invalid) makes the software easier to use and more flexible.

SUMMARY

The present approach to programming pump configuration files provides flexibility by permitting the operator to set a parameter to an invalid value and later correct the invalidity condition by changing at least one of the settings causing the invalidity condition. The principles of the present disclosure, which may be embodied as an insulin pump configuration software application, also include features for notifying the operator that an invalidity condition exists, and assisting the operator in correcting the condition. Moreover, the risk of programming a pump with an invalid parameter setting is managed by preventing the operator from programming a pump when an invalidity condition exists.

In an exemplary embodiment of the present disclosure, there is disclosed a method for configuring an insulin pump. The method includes the step of initiating a workflow for setting parameters of an insulin pump configuration file. The method further includes the step of receiving a setting of a first parameter. The method further includes the step of receiving a user-selected setting of a second parameter that is dependent upon the setting of the first parameter. The method further includes the step of determining whether the setting of the second parameter is invalid based on the setting of the first parameter. The method also includes the steps of permitting the workflow to continue when the setting of the second parameter is invalid, displaying a confirmation screen, and after displaying the confirmation screen, permitting the user to correct the setting of one of the first parameter and the second parameter to cause the setting of the second parameter to be valid. In a variation of the disclosed method, the displaying step includes the steps of displaying an icon indicating that the setting of the second parameter is invalid, and providing directions to the user for correcting the invalid setting when a screen pointer is placed over the icon. In another variation, the method further includes the step of displaying an icon indicating that the setting of the second parameter is invalid upon determining that the setting of the second parameter is invalid. In yet another variation, the method further includes the step of permitting the user to save the configuration file before correcting the setting of the one of the first parameter and the second parameter. In an extension of this variation, the configuration file is saved to the insulin pump over a communication link. In still another variation, the first parameter relates to a basal rate profile. In another variation, the method further includes the step of responding to a request from the operator to save the configuration file including the invalid setting of the second parameter by preventing the operator from saving the configuration file to the insulin pump. In yet another variation, the configuration file includes a plurality of basal rate profiles. In an extension of this variation, the method further includes the step of prompting the operator to set a parameter associated with one of the basal rate profiles by displaying a thumbnail image of each of the basal rate profiles.

In another exemplary embodiment of the present disclosure, there is disclosed a computer readable medium tangibly embodying a program of instructions executable by a computing device to perform method steps including prompting an operator to activate a configuration file for controlling the operation of an insulin pump. The configuration file includes a first parameter having a first setting and a second parameter having a second setting. The first and second settings being related to one another by a rule. The method steps also include the step of permitting the operator to change the first and second settings in any order, even when a change causes an invalidity condition based on the rule. The steps further include the step of providing visual feedback to the operator when a change in one of the first and second settings causes an invalidity condition. Finally, the method steps include the step of preventing the operator from saving the activated configuration file to the pump as long as an invalidity condition exists.

In still another exemplary embodiment of the present disclosure, there is disclosed a system for programming an insulin pump. The system includes a computing device having a display and a memory location and software stored in the memory location for execution by the computing device. The software facilitates a workflow for setting parameters of a configuration file that controls operation of the pump. The workflow including the step of prompting an operator to activate the configuration file. The workflow also includes the step of displaying a representation of a first parameter on the display. The workflow also includes the step of responding to the operator's selection of the first parameter by enabling the operator to change an original value for the first parameter. Additionally, the workflow includes the step of determining that the changed value is invalid because the changed value violates a rule relating the first parameter to a second parameter. The workflow further includes the step of maintaining the changed value in the active configuration file. The workflow also includes the step of displaying an invalid item icon on the display in association with the changed value. Finally, the workflow includes the step of responding to a request from the operator to save the active configuration file including the changed value by preventing the operator from saving the active configuration file to the pump. In a variation thereof, the workflow further includes the step of displaying a settings report to the operator, wherein the settings report includes a configuration file tree structure that identifies the first parameter, an active file information column including the original value of the first parameter, and a modified file information column including the changed value of the first parameter. In an extension of this variation, the settings report further includes a first invalid item icon associated with the changed value. In a further extension, the settings report includes a second invalid item icon associated with the second parameter. In another variation thereof, the software is configured to automatically position the configuration file tree structure such that the changed value is located in a viewable area of the display. In yet another variation, the determining step further includes the step of displaying on a status bar an indication that the changed value is invalid. In another variation, the workflow further includes the step of permitting the operator, after the maintaining step, to modify one of the changed value and a value of the second parameter so that the rule is no longer violated. In an extension of this variation, the workflow further includes the step of responding to a request from the operator to save the active configuration file when the rule is no longer violated by prompting the operator to select one of the pump and the memory location as a destination for the active configuration file. In another extension, the workflow further includes the step of prompting the operator to confirm the change of the value from the original value to the changed value. In yet a further extension, the prompting the operator to confirm step includes the step of displaying a representation of the original value and the changed value.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, wherein.

Corresponding reference characters indicate corresponding parts throughout the several views.

DETAILED DESCRIPTION

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

It should be understood that although the concepts below are described as relating to insulin pump configuration software, such as the ACCU-CHEK® Insulin Pump Configuration Software provided by Roche Diagnostics Corporation, the concepts may also relate to diabetes management software systems for tracking and analyzing health data, such as, for example, the ACCU-CHEK® 360° product provided by Roche Diagnostics Corporation. Moreover, the concepts described herein may also have applicability to apparatuses, methods, systems, and software in fields that are unrelated to healthcare. Furthermore, it should be understood that references in this patent application to devices, pumps, meters, monitors, or related items are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics Corporation or divisions thereof.

Figure 1:
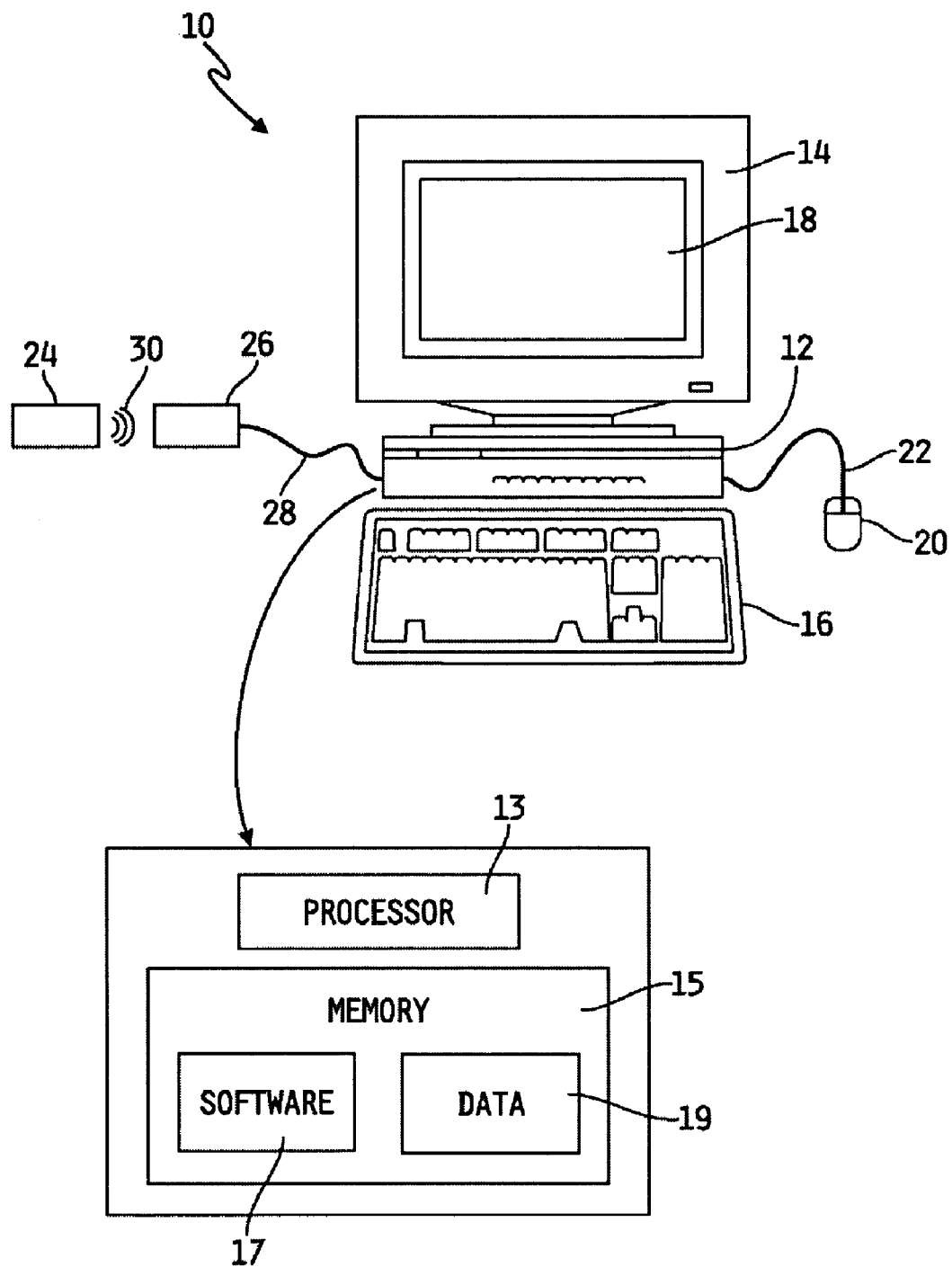
FIG. 1 is a conceptual diagram of a computing device in communication with an insulin pump.

Turning now to the figures, FIG. 1 depicts an exemplary embodiment of a system 10, some or all of the components of which may be used in conjunction with the teachings of the present disclosure. System 10 generally includes a computing device 12, shown here in the form of a computer having display device 14, in this case a computer video screen or monitor having screen 18, a keyboard 16, a processor 13, and memory 15, which may contain the software 17 of the present disclosure and data 19 as is further described herein. While described and depicted herein with specific reference to a computer, certain concepts of the present disclosure may be utilized in conjunction with any computing device capable of operating pump programming software. Computing device 12 also has a pointing device or mouse 20 connected to it by cable 22 (or wirelessly). While mouse 20 and keyboard 16 are shown, system 10 may include any input device such as a touchpad, joystick, touch screen, trackball, etc.

Computing device 12 may include a variety of computer-readable media. Computer-readable media can be any available media that can be accessed by computing device 12 and includes both volatile and non-volatile media, and removable and non-removable media. By way of example, and not limitation, computer-readable media may comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules and other data and which can be accessed by computing device 12. Computer-readable media may be accessed directly or through a network such as the Internet.

System 10 is configured to provide information to, and receive information from, infusion pump 24. Again, while an infusion pump, and more particularly an insulin pump, is described herein, it should be understood that the teachings of the present disclosure may also apply to devices such as "smart" insulin pens or other such devices known or hereafter developed. In FIG. 1, computing device 12 is shown coupled to communication media or dongle 26, in this case a modulated signal transceiver, accessible to computing device 12 by means of cable 28, and configured to transmit and receive modulated signal 30 to establish logical communication with pump 24. In another exemplary embodiment, computing device 12 and pump 24 may include ports configured to establish a physical connection. By way of example, and not limitation, dongle 26 may include wired media such as a wired network or direct wired connection, and wireless media such as acoustic, RF, infrared and other wireless media. More specifically, dongle 26 as depicted includes an infrared port for communication with a similar infrared port of pump 24.

Figure 2:
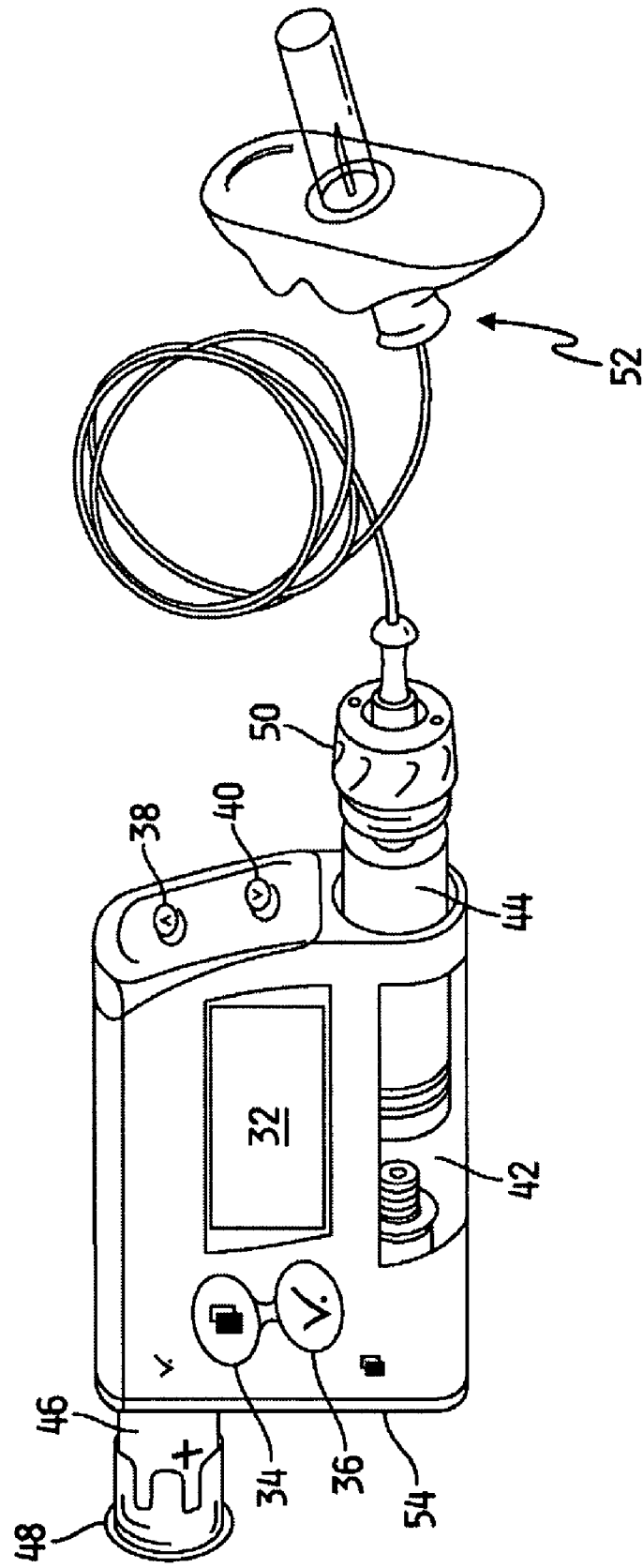
FIG. 2 is perspective view of an insulin pump coupled to an infusion set.

Referring now to FIG. 2, pump 24 includes a display 32 for displaying information to an operator or user, a menu button 34 for navigating though the various functions provided by pump 24, a check button 36 for selecting options, an up key 38 and down key 40 for scrolling through options and controlling certain insulin delivery functions, a cartridge receptacle 42 for storing an insulin cartridge 44, a battery 46 (shown partially inserted), a battery cap 48 (shown unsecured to pump 24), an adapter 50 for physically coupling cartridge 44 to an infusion set 52, and a communication port 53 for sending information to, or receiving information from, computing device 12 through dongle 26.

Figure 3:
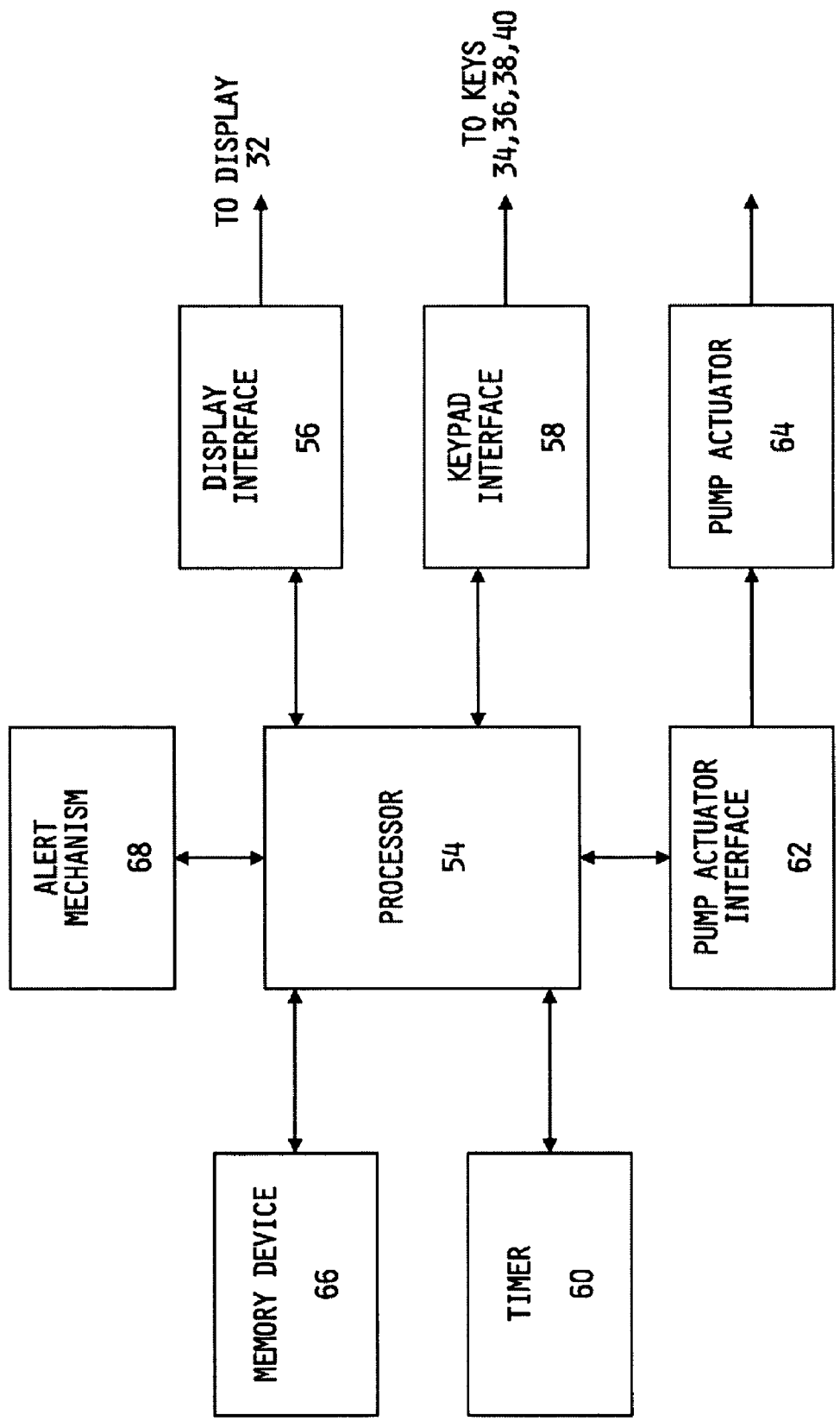
FIG. 3 is a block diagram of internal components of the pump of FIG. 2.

FIG. 3 provides a block diagram representation of internal components of pump 24. As shown, pump 24 includes a processor 54 coupled to a display interface 56, which is coupled to display 32. Processor 54 is also coupled to a keypad interface 58 which is coupled to keys 34, 36, 38, 40, and a pump actuator interface 62 which is coupled to an actuator 64 suitable for delivering insulin doses (medical infusion pumps other than insulin pumps will deliver doses of other medicament). Processor 54 is further coupled to a memory device 66 that stores application programs and data, including the configuration files described herein. Memory device 66 is constructed of any combination of volatile and/or nonvolatile memory suitable for a particular embodiment. Processor 54 is also coupled to an alert mechanism 68, that, in various embodiments is a buzzer, a vibrator, a light emitting diode, or the like, suitable for providing audible, tactile, or visual alerts to an insulin pump user. Finally, processor 54 is coupled to a timer 60, which is capable of maintaining a current time, including time of day and day of the week.

For the purpose of the illustrative example of the operation of software 17, assume the operator is a health care provider who wishes to change the maximum hourly basal rate for a user of pump 24 based on new information regarding the user's health condition. As will be described below, in this example scenario, the operator will read a configuration file from pump 24 and change the maximum hourly basal rate for the user. Software 17 will permit the operator to make this change, even though the changed value is invalid because hourly basal rates included in the basal rate profiles of the configuration file exceed the new maximum value. The manner in which the operator is alerted to the invalidity and permitted to correct it is also described below.

Figure 4:
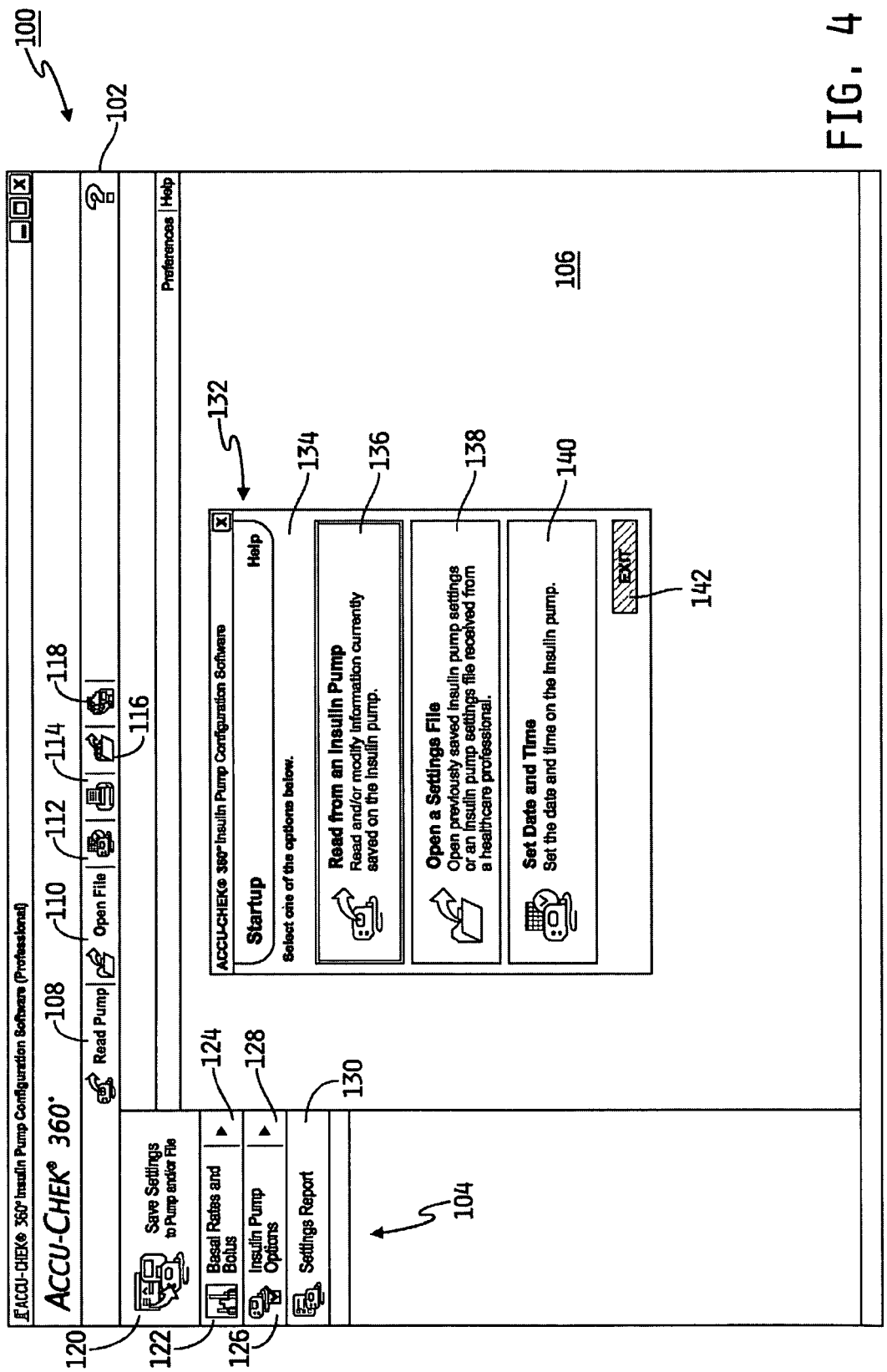
FIG. 4 is a screenshot of a home screen displayed upon activation of software according to teachings of the present disclosure.

FIG. 4 depicts the home screen 100 displayed upon activation of software 17. Home screen 100 generally includes a toolbar 102, a navigation menu 104, and an active window 106. Toolbar 102 includes a read pump icon 108, an open file icon 110, a date/time icon 112, a print icon 114, a load all profiles from file icon 116, and a save all profiles to a file icon 118. Navigation menu 104 includes a save settings button 120, a basal rates and bolus button 122 with an indicator 124 denoting the existence of a dropdown menu associated with button 122, an insulin pump options button 126 with a similar indicator 128, and a setting report button 130. The content of active window 106 changes depending upon the operation being performed by software 17. Here, active window 106 includes a start up dialog box 132.

Start up dialog box 132 includes a message area 134, a read pump button 136, an open file button 138, a set date/time button 140, and an exit button 142. For the purpose of this description, the operator will be described as obtaining an insulin pump configuration file from pump 24 using read pump button 136. As is further described herein, the process for saving a configuration file to pump 24 or to memory 15 on computing device 12 differs. The process for obtaining or retrieving a configuration file from either pump 24 or memory 15 on computing device 12, however, is not meaningfully different for the purpose of the present disclosure. The operator begins the process of obtaining a configuration file from pump 24 by activating read pump button 136.

Figure 5:
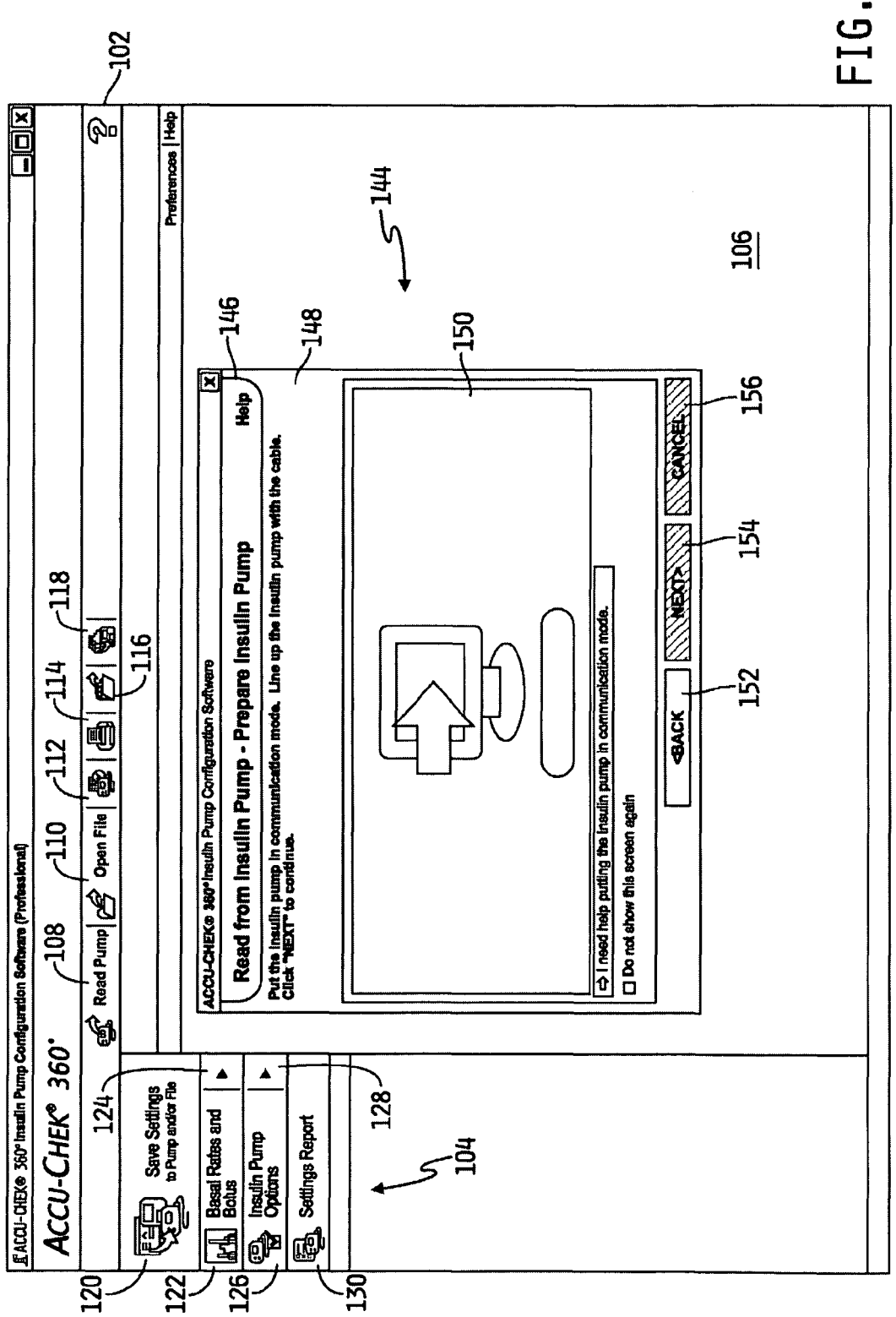
FIGS. 5 and 6 are screenshots including a communication status dialog box.

As is shown in FIG. 5, when the operator activates read pump button 136, start up dialog box 132 in active window 106 is replaced by communication status dialog box 144. Communication status dialog box 144 includes a title bar 146 which describes the operation being performed, a message area 148 which may provide instructions to the operator for performing the operation, a status window 150 which provides graphical and/or textual information about the operation, a back button 152, a next button 154 and a cancel button 156. As shown in the figure, the operator is provided instructions in message area 148 for preparing pump 24 for communications with computing device 12. As explained above, a variety of different communication technologies may be employed to facilitate this communication. In this example, the operator is instructed to place pump 24 in communication mode and align pump 24 with dongle 26 for IR communications with computing device 12. When pump 24 is prepared for communications, the operator activates next button 154.

Figure 6:
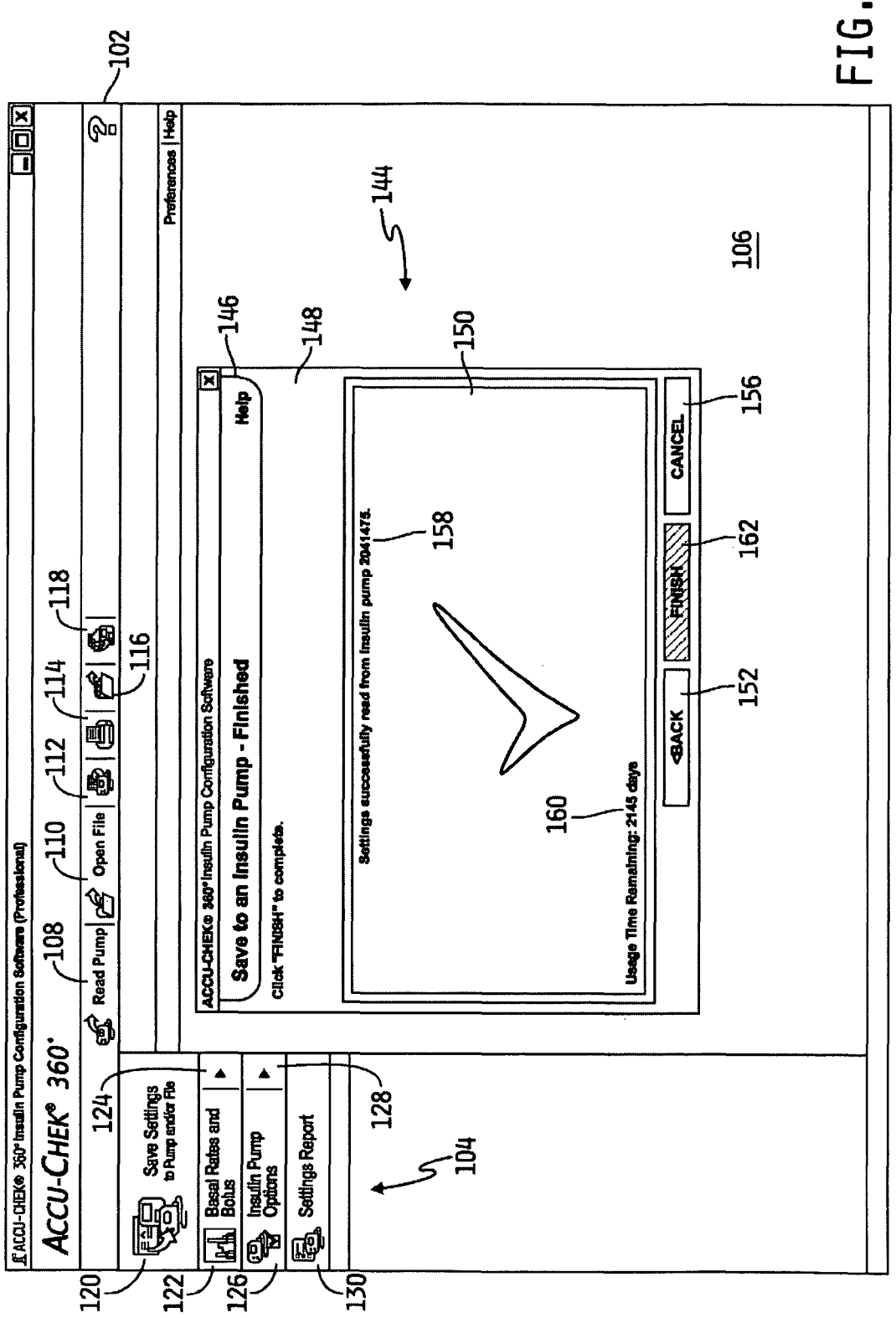

FIG. 6 depicts communication status dialog box 144 after the communication file is read from pump 24. As shown, title bar 146 indicates that communications are complete, as does message area 148. Status window 150 of communication status dialog box 144 provides a message 158 to the operator indicating the serial number of pump 24 and a counter message 160 indicating the number of days pump 24 may be considered operational. The operator proceeds by activating finish button 162.

Figure 7:
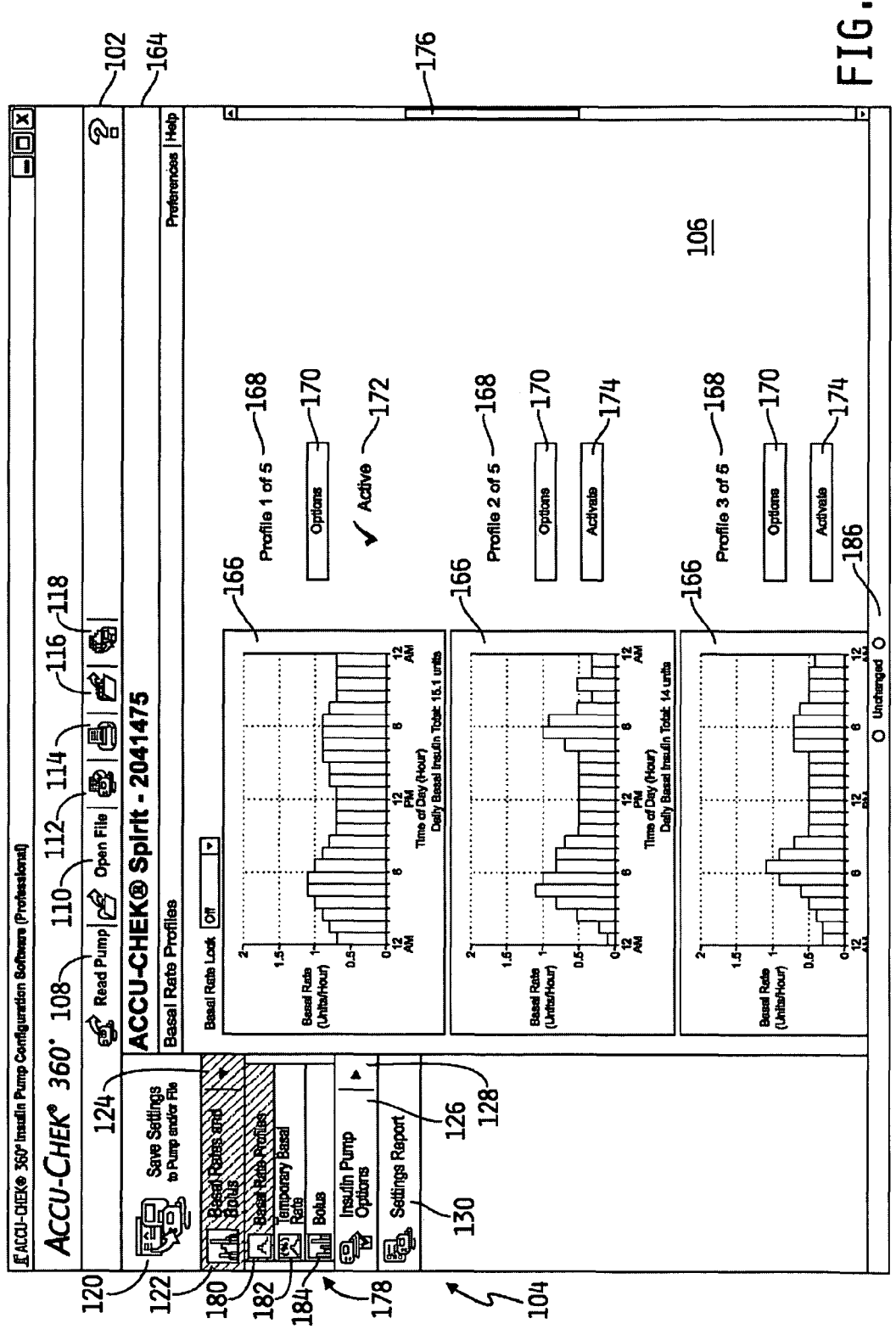
FIG. 7 is a screenshot of a display generated upon activating a configuration file.

After the configuration file is loaded onto computing device 12, the operator is provided information in active window 106 regarding the basal rate profiles included in the configuration file as depicted in FIG. 7. In the depicted context, active window 106 includes a title bar 164 that identifies pump 24 by name and serial number, at least one profile thumbnail image 166 that functions as a graphic preview of the data associated with a basal rate profile included in the configuration file, at least one profile indicator 168 indicating the number of the corresponding basal rate profile represented by the associated thumbnail image 166, at least one options button 170, and an active icon 172 and/or an activate button 174. In one embodiment of the present disclosure, the configuration file includes five basal rate profiles. Accordingly, as depicted in the figure, a thumbnail image 166, profile indicator 168, options button 170, and an active icon 172 and/or an activate button 174 is displayed for each of the file basal rate profiles. The operator may view basal rate profile information not shown in active window 106 by using scroll bar 176. By default, the first depicted basal rate profile is designated as active by software 17. As such, active icon 172 is shown in association with thumbnail image 166 instead of activate button 174. The operator may select other available basal rate profiles to be made active by selecting the activate button 174 associated with the desired basal rate profile. As is also shown in FIG. 7, when a configuration file is read or opened and active window 106 is populated with basal rate profile information, basal rate and bolus button 122 is automatically activated, causing the display of dropdown menu 178 in navigation menu 104.

Dropdown menu 178 includes a basal rate profile button 180 (which is depicted as active), a temporary basal rate button 182, and a bolus button 184. In the example that follows, basal rate profile information will be modified to illustrate the principles of the present disclosure for invalid settings notification and correction. It should be understood, however, that many different settings included in the configuration file are dependent upon one or more other settings, and that modification of one setting may cause an invalidity condition resulting from the value of other settings. The invalid settings notification and correction principles described below apply equally to these other settings, which may be accessed and modified using temporary basal rate button 182, bolus button 184, various options presented upon activation of insulin pump options button 126, or other navigation paths provided by software 17. Finally, active window 106 further includes a status bar 186 which indicates the status of the currently active configuration file. Here, the status is unchanged.

Figure 8:
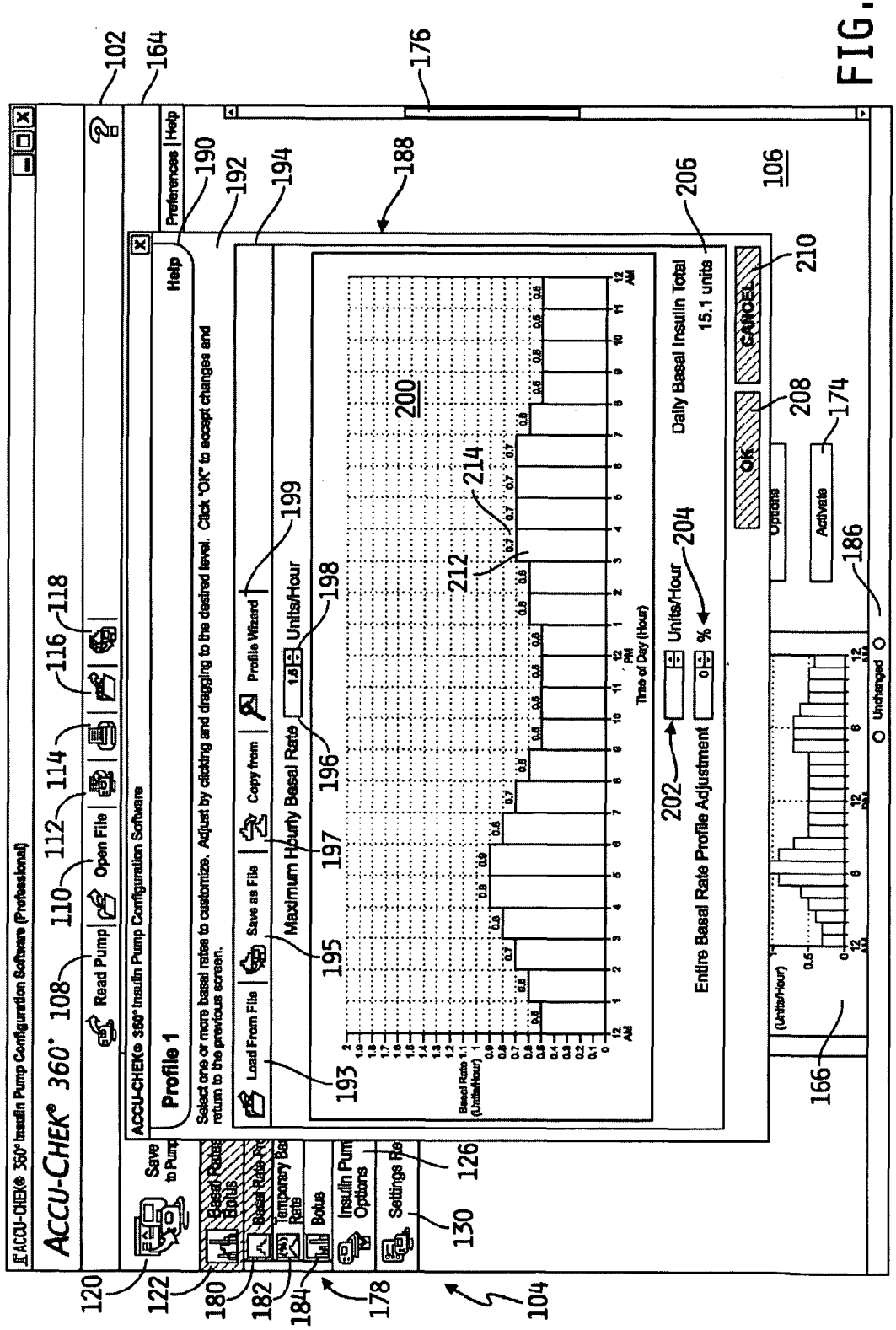
FIGS. 8-10 are screenshots of a display depicting a profile edit window generated upon selecting a basal rate profile.

To begin modifying one of the basal rate profiles included in the active configuration file, the operator activates an options button 170 associated with the profile. FIG. 8 depicts the result of activating options button 170 associated with profile one depicted in FIG. 7. As shown, a pop-up profile edit window 188 is displayed to the operator. Edit window 188 includes a title bar 190 identifying the active profile, an instructions area 192 that provides information about modifying parameters of the active profile, a tool bar 194, a maximum hourly basal rate text field 196 and associated up/down arrows 198, a profile graph 200, a group rate adjustment area 202, a profile adjustment area 204, a total dose indicator 206, an OK button 208 and a cancel button 210. Toolbar 194 includes load from file button 193, save as file button 195, copy from button 197, and profile wizard button 199, the operation of which is described in co-pending patent application entitled "INSULIN PUMP PROGRAMMING SOFTWARE WITH BASAL PROFILE PREVIEW FEATURE," Ser. No. 12/205,570, the entire contents of which is hereby expressly incorporated herein by reference.

Profile graph 200 includes bar chart representations of hourly basal rates 212 for each of 24 hours in a day. Value labels 214 are associated with each hourly basal rate 212. As is well understood in the art, pump 24 delivers insulin to the user substantially continuously. Various physiological factors influence the appropriate amount of insulin to deliver to the user, and the appropriate delivery rate fluctuates throughout the day. By manipulating profile graph 200 and/or using other controls provided on edit window 188, the operator may make changes to any of hourly basal rates 212. The techniques facilitated for making such adjustments, and the operation of group rate adjustment area 202 and profile adjustment area 204 are described in detail in co-pending patent application entitled "USER INTERFACE FOR MANIPULATING GROUPS OF DATA REPRESENTATIONS OF A GRAPHICAL DISPLAY," Ser. No. 12/205,582, (hereinafter, "the Data Manipulation Application"), the entire contents of which are hereby expressly incorporated herein by reference.

One example of the dependency of one configuration file parameter on another is the relationship between hourly basal rates 212 and the maximum hourly basal rate. More specifically, none of the hourly basal rates 212 of the various basal rate profiles included in a configuration file can exceed the maximum hourly basal rate. If, using a conventional system, an operator attempted to set the maximum hourly basal rate parameter to a value below an hourly basal rate 212, the system would prevent the operator from proceeding through the configuration file adjustment workflow. The operator would be prevented from setting such a maximum value because to permit the setting would violate the relationship rule that no hourly basal rate 212 exceed the maximum. The only way in which the operator could set the low maximum value would be to first change the values of the hourly basal rates 212 that exceed the new, desired maximum. This approach requires the operator to follow a sequential set of steps for making adjustments to configuration file parameters wherein no setting can violate a relationship rule relating to a previously defined parameter setting. For the illustrative example provided herein, the operator will set the maximum hourly basal rate parameter to an invalid value that is less than one or more predefined settings of hourly basal rates 212.

Figure 9:
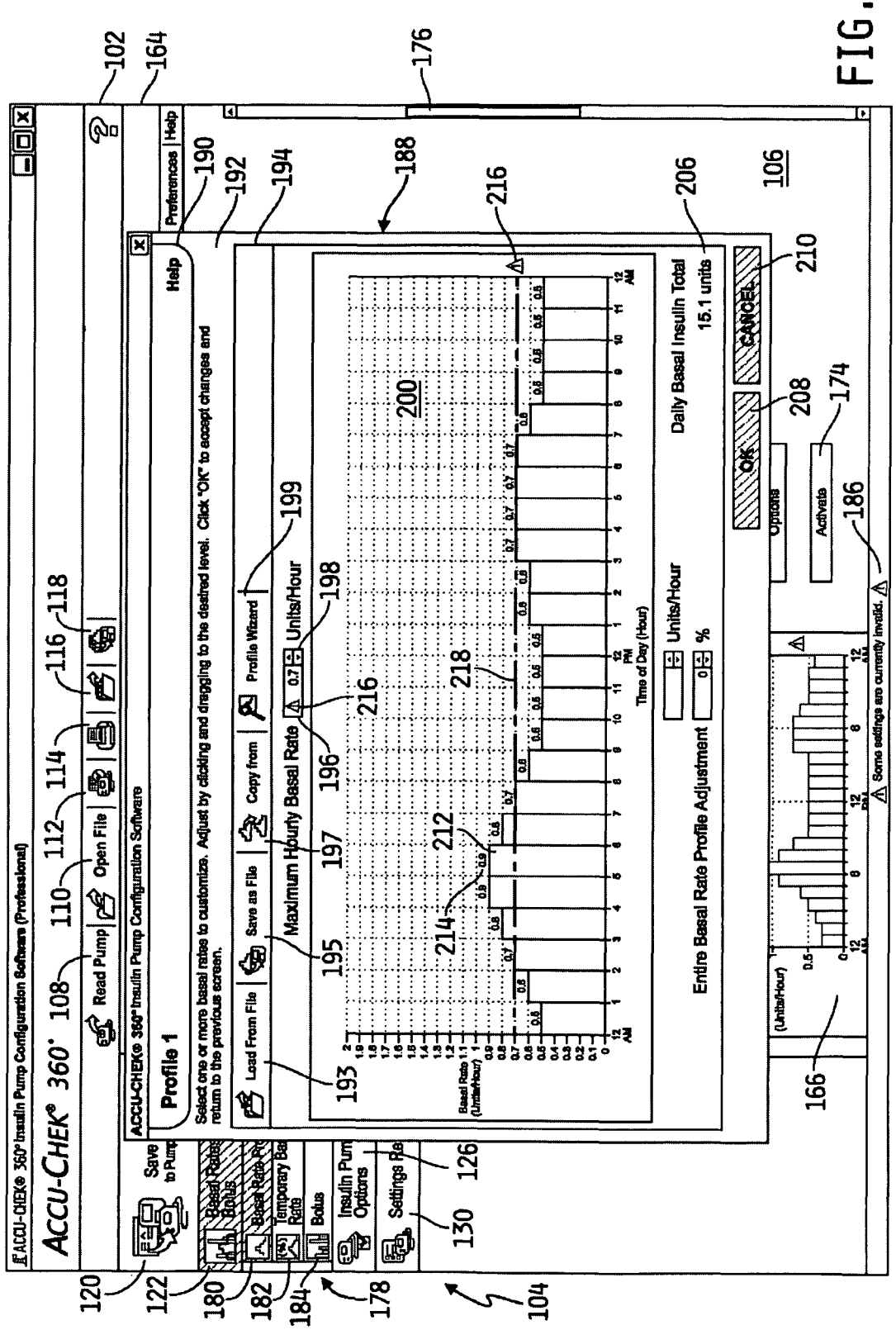

As shown in FIG. 8, maximum hourly basal rate text field 196 indicates a maximum of 1.5 units/hour. By using down arrow 198 associated with maximum hourly basal rate text field 196, the operator adjusts the maximum rate to a value of 0.7. The resulting display is shown in FIG. 9. As shown, although the operator is permitted to define a maximum value of 0.7, an invalid item icon 216 is displayed in text field 196. Additionally, a threshold indicator 218 is depicted on profile graph 200 corresponding to the newly defined maximum value. A second invalid item icon 216 is also displayed adjacent threshold indicator 218. Moreover, status bar 186 now indicates that an invalidity condition exists.

At this point in the described workflow, the operator may save the configuration file, including the invalid setting for maximum hourly basal rate, to memory 15 on computing device 12 by activating save as file button 195. It should be understood, however, that the operator is not permitted to save the configuration file to pump 24 without first correcting the invalidity condition of the maximum hourly basal rate. It may be desirable to save a configuration file to computing device 12 even though an invalidity condition exists if, for example, the operator wishes to attend to other tasks before taking the time to correct the invalidity condition. The file may be saved, then later retrieved and corrected according to the operator's schedule.

Figure 10:
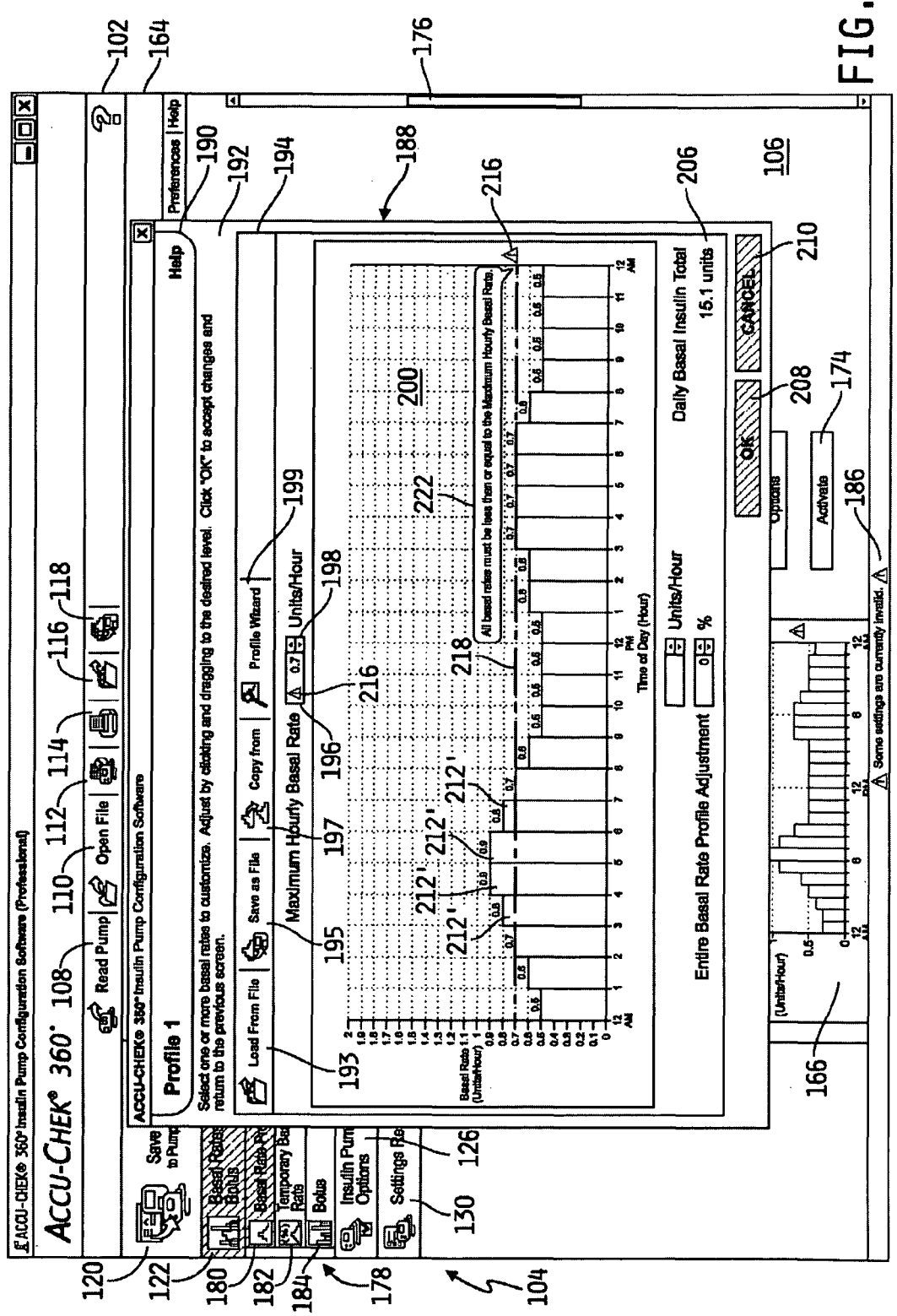

FIG. 10 depicts a mouseover message 222 that appears when the operator hovers over any of invalid item icons 216 using a pointing device. Mouseover message 222 provides information about the invalidity condition to assist the operator in correcting it. It should be understood that mouseover message 222 may be configured as a link which, when activated by the user, causes software 17 to divert operation of the workflow to the appropriate location for correcting the invalidity condition. Here, the operator may correct the invalidity condition for profile 1 by selecting hourly basal rates 212' that exceed the maximum hourly rate and adjusting them downwardly in the manner described in the Data Manipulation Application.

Figure 11:
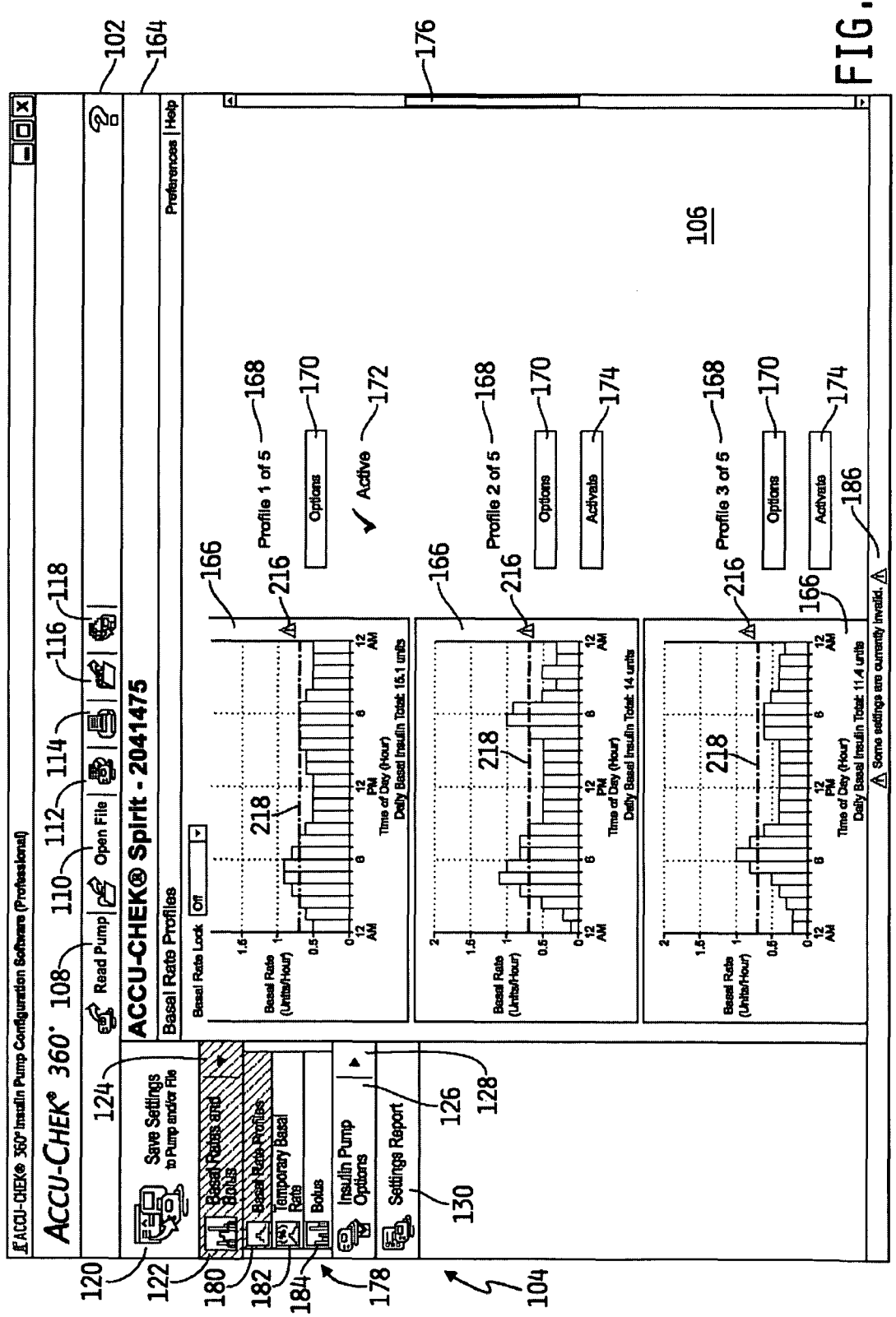
FIG. 11 is a screenshot similar to that of FIG. 7, but indicating the presence of an invalidity condition.
Figure 12:
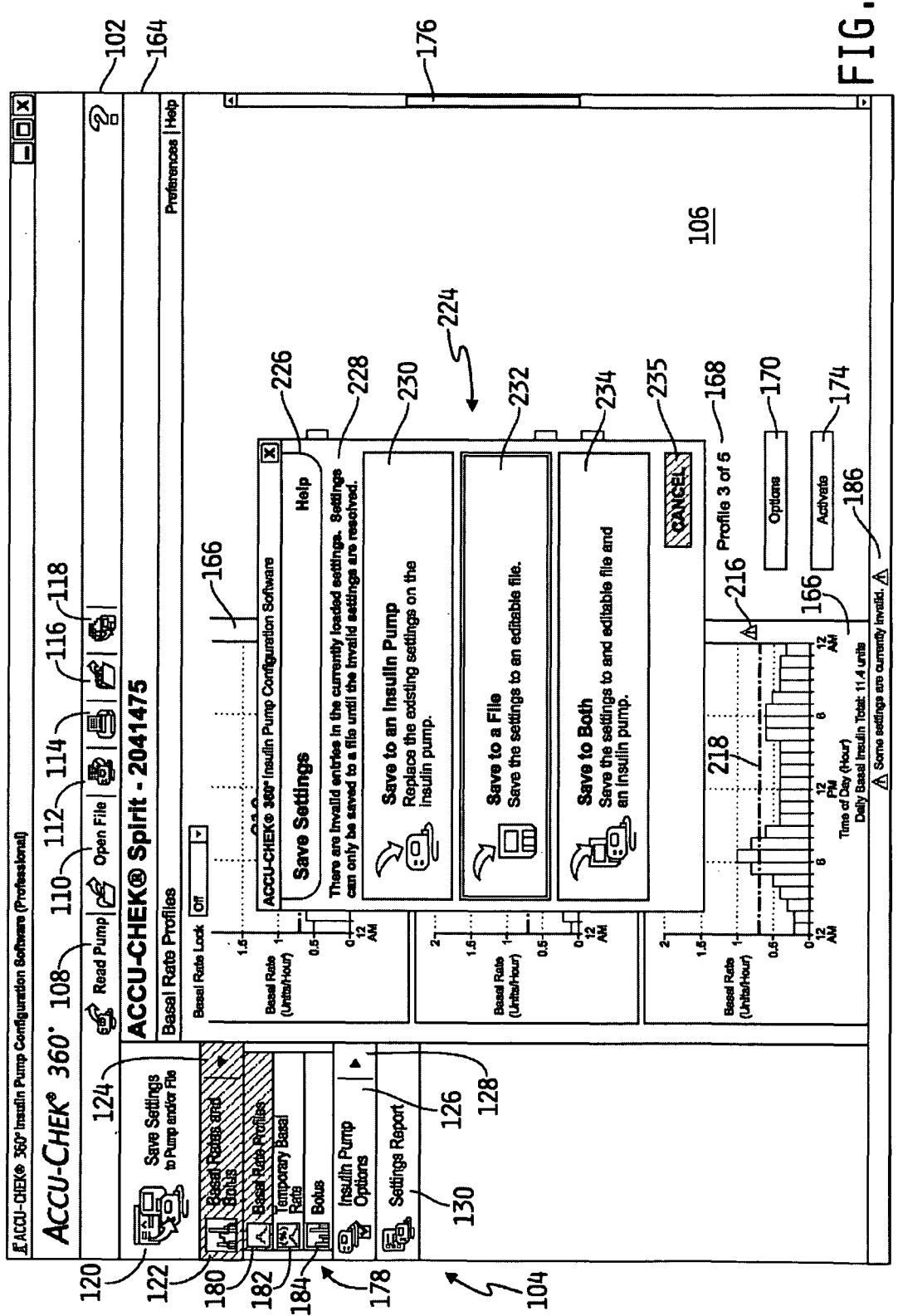
FIG. 12 is a screenshot including a save settings dialog box.

Assuming that the operator wishes to proceed with the workflow and activates OK button 208, FIG. 11 is displayed. FIG. 11 is substantially the same display as that depicted in FIG. 7, except that thumbnail images 166 of FIG. 11 corresponding to basal rate profiles having an invalid parameter setting include threshold indicators 218 and invalid item icons 216. Additionally, status bar 186 indicates the existence of an invalidity condition. The operator may activate any of options buttons 170 to activate a profile and correct the associated invalidity condition. In this example, assume that the operator activates save settings button 120 of navigation menu 104. In that case, a pop-up save settings dialog box 224 is displayed over active window 106 as shown in FIG. 12.

Dialog box 224 includes a title bar 226, a message area 228, a save to pump button 230, a save to file button 232, a save to both button 234, and a cancel button 235. As shown, message area 228 informs the operator that the active configuration file includes invalid parameters and can only be saved to a file stored on computing device 12. Accordingly, save to pump button 230 and save to both button 234 are depicted as being inactive. For this example, assume the operator decides to correct the invalidity condition without saving the active configuration file, and activates cancel button 235.

Figure 13:
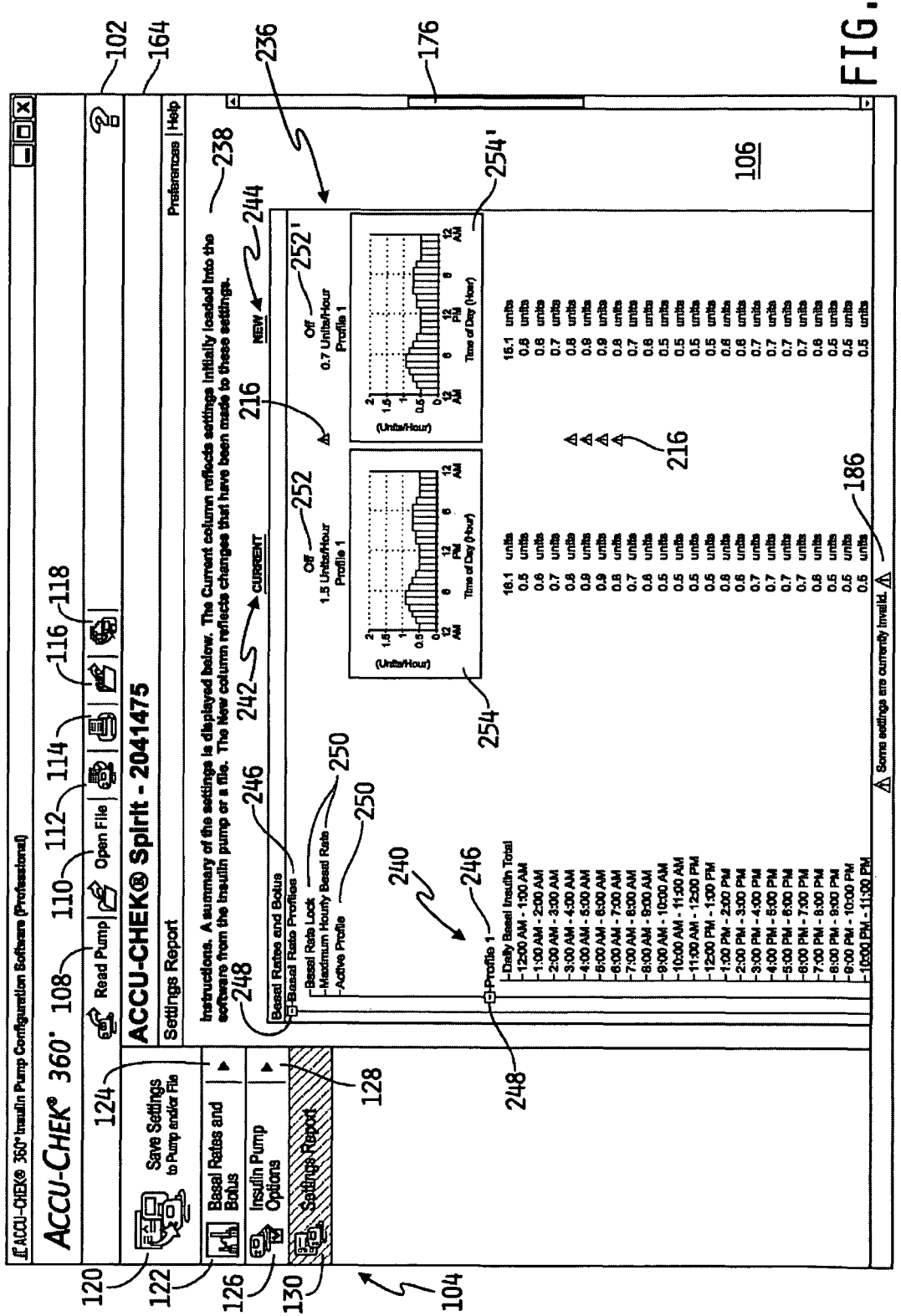
FIG. 13 is a screenshot including a settings report window.

As depicted in FIG. 13, active window 106 is then populated with a settings report window 236. Settings report button 130 of navigation menu 104 is depicted as active. Settings report window 236 generally includes an instructions area 238, a configuration file tree structure 240, an active file information column 242, and a modified file information column 244. Configuration file tree structure 240 includes a plurality of different parameter titles 246 accompanied by expander icons 248 that, when activated, cause the display of parameter names 250 associated with the parameter title 246. Active file information column 242 includes data fields 252 corresponding to each displayed parameter name 250. In this example, data fields 252 include the status or value of the named parameter as originally uploaded from pump 24. Active file information column 242 may further include thumbnail images 254 that graphically depict the data associated with basal rate profiles. Modified file information column 244 similarly includes data fields 252' and thumbnail images 254' that reflect the changes made to the configuration file parameters during the present workflow.

As also shown in FIG. 13, parameters that are different (current vs. new) are highlighted in settings report window 236. Parameters that have been affected by an invalidity condition are both highlighted and accompanied by an invalid item icon 216. When the operator hovers a pointing device over any of invalid item icons 216, a mouseover message 222 (not shown) as shown in FIG. 10 is displayed to the operator.

Here, invalid item icons 216 are displayed adjacent data fields 252, 252' corresponding to parameter name 250 for maximum hourly basal rate and various hourly basal rates of profile 1. The operator can scroll through the information presented in settings report window 236 using scrollbar 176.

Although not apparent from FIG. 13, software 17 is configured to automatically position the information in settings report window 236 such that invalidly set parameters may be viewed without having to use scrollbar 176. Additionally, when more invalidly set parameters are present than can be simultaneously displayed in the viewable area of settings report window 236, software 17 is configured to prioritize the invalidly set parameters and automatically position the information such that the most important invalidly set parameters (i.e., the parameters most likely to affect the safe operation of pump 24) are displayed in the viewable area of settings report window 236.

Figure 14:
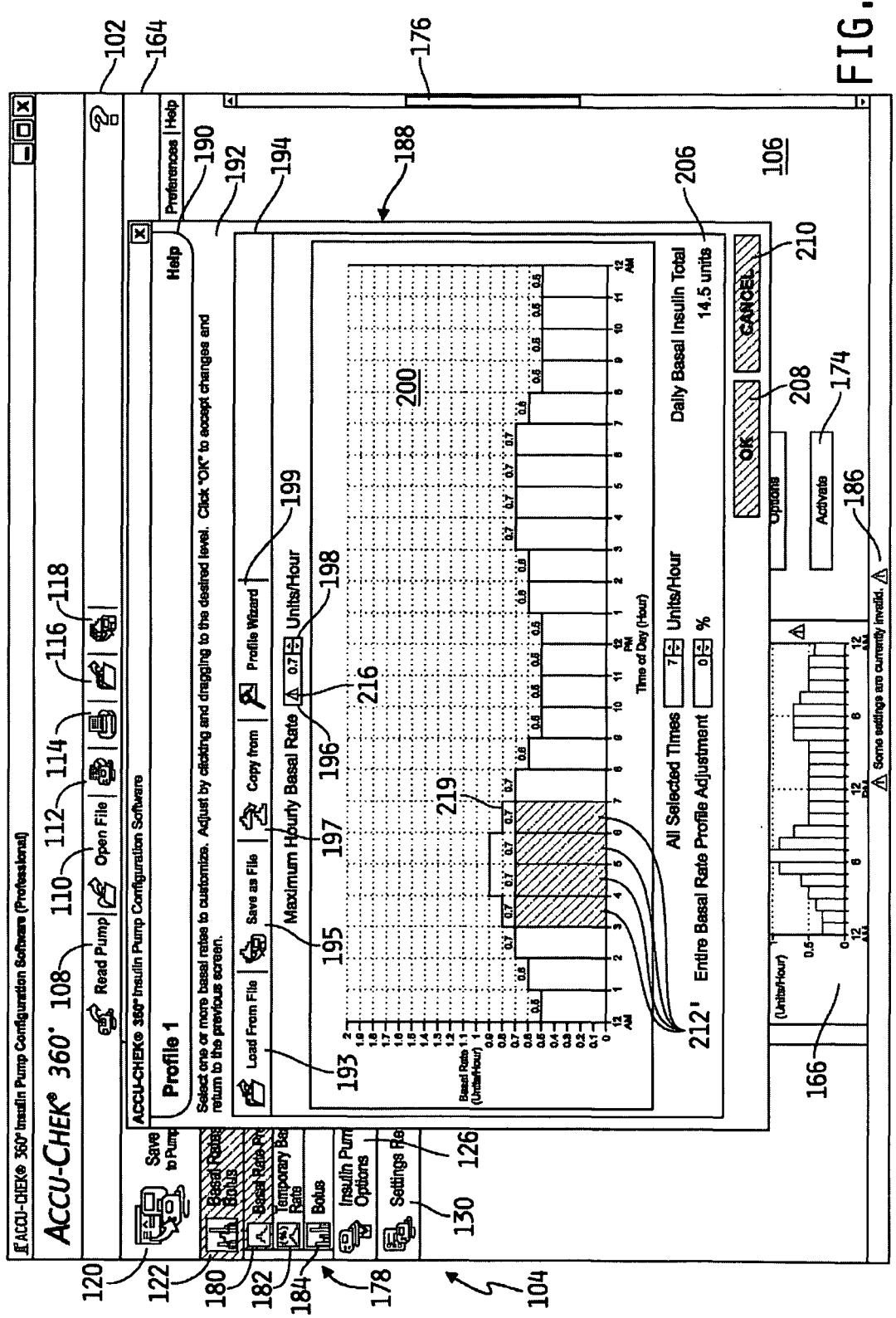
FIG. 14 is a screenshot depicting an edit profile window similar to that of FIG. 10.

To correct the illustrative invalidity conditions indicated on settings report window 236, the operator activates basal rates and bolus button 122 of navigation menu 104, which returns the operator to the display of FIG. 11. Upon activating options button 170 associated with profile 1 of 5, the operator returns to the display of FIG. 10, which depicts, among other things, the setting of maximum hourly basal rate to 0.7. The operator may correct the invalidity condition by selecting hourly basal rates 212' for 3:00 a.m. through 6:00 a.m. and adjusting them downwardly in the manner described in the Data Manipulation Application. The resulting display is shown in FIG. 14. As shown, hourly basal rates 212' have been set to 0.7, a value that does not exceed the maximum hourly basal rate. Accordingly, threshold indicator 218 is no longer displayed. A prior value indicator 219 is, however, displayed to provide a visual indication of the original value of hourly basal rates 212'. Invalid item icon 216 is displayed in maximum hourly basal rate text field because other profiles in the active configuration file still contain hourly basal rates 212 that exceed this maximum value. Status bar 186 still indicates an invalidity condition for the same reason. Also, total dose indicator 206 now shows 14.5 units instead of 15.1.

Figure 15:
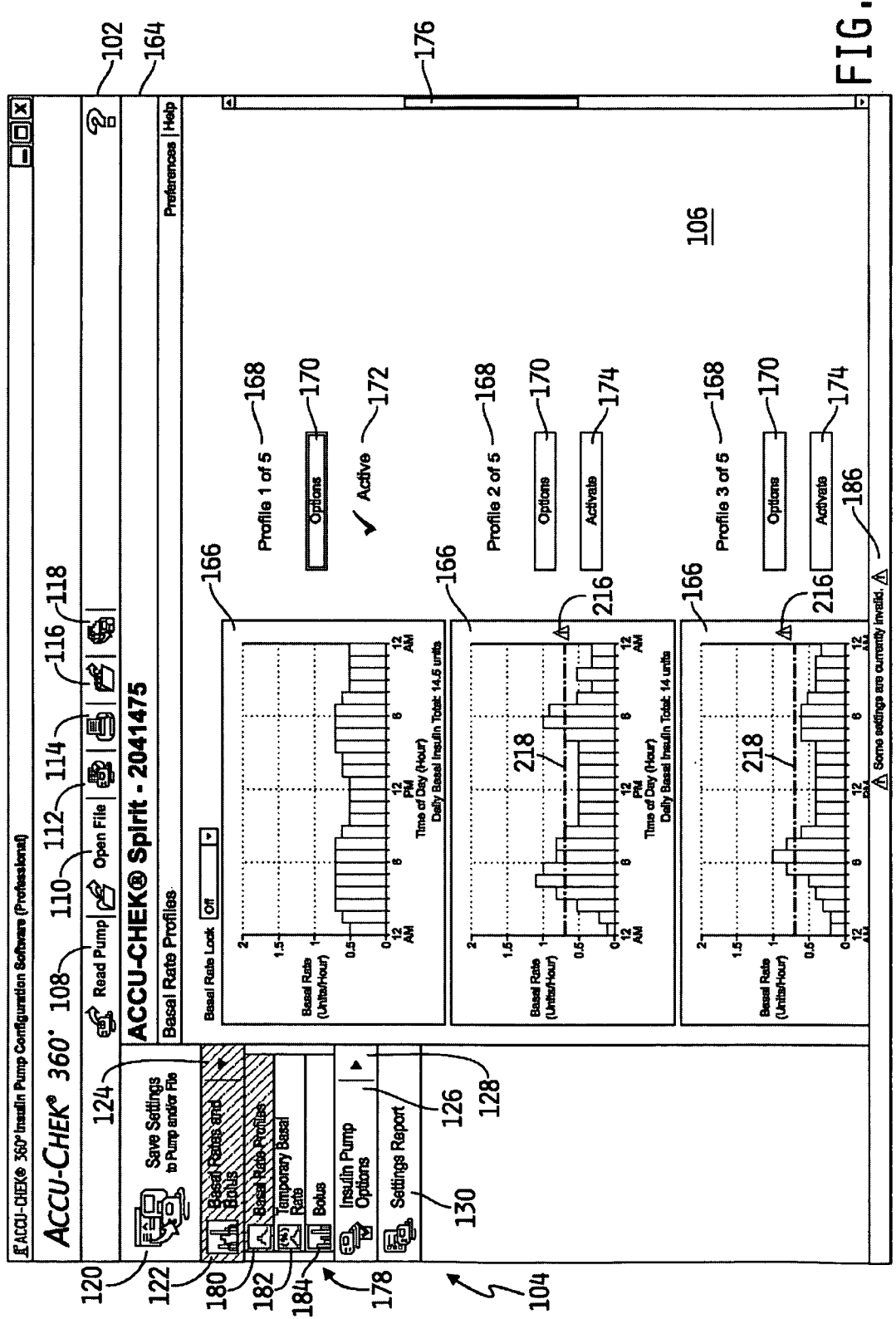
FIG. 15 is a screenshot similar to that of FIG. 11, but indicating the absence of an invalidity condition.

After the operator corrects the invalidity condition for profile 1 and activates OK button 208, FIG. 15 is displayed. FIG. 15 is almost identical to FIG. 11, except that the thumbnail image 166 corresponding to profile 1 no longer indicates an invalidity condition. The thumbnail images 166 for profiles 2 and 3, however, still indicate an invalidity condition. The operator may correct the invalidity condition by activating each of the other profiles and adjusting the hourly basal rates in the manner described above.

Figure 16:
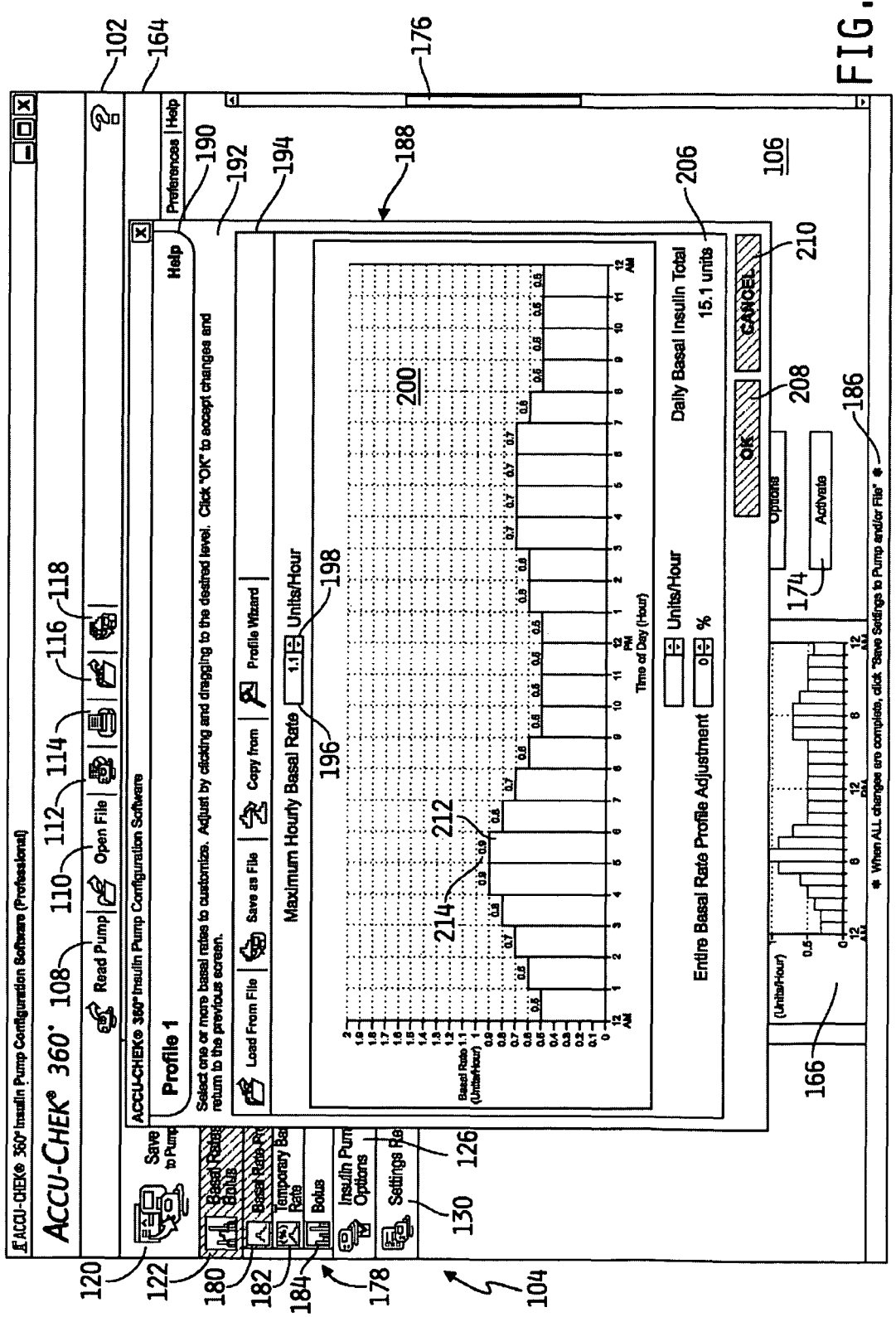
FIG. 16 is a screenshot similar to that of FIG. 9, but indicating the absence of an invalidity condition.

Alternatively, instead of adjusting hourly basal rates 212' as described above, the operator may correct the above-described invalidity condition by adjusting the maximum hourly basal rate. Referring again to FIG. 9, the operator may use up/down arrows 198 to adjust the maximum hourly basal rate to 1.1, causing the display of FIG. 16. As shown in FIG. 16, threshold indicator 218 and invalid item icons 216 are no longer present. Additionally, status bar 186 no longer indicates an invalidity condition, but instead instructs the operator to save the settings when changes are complete.

Figure 17:
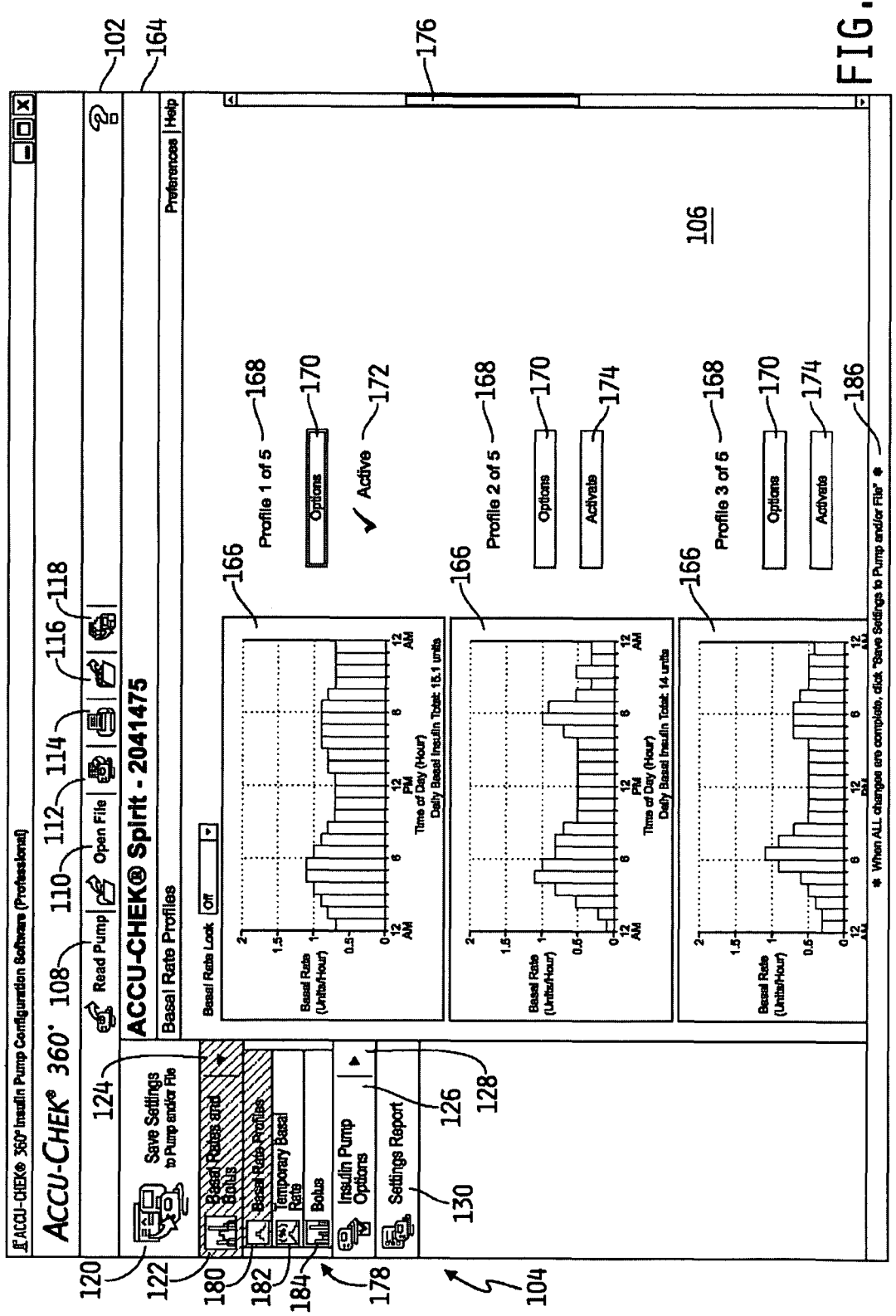
FIG. 17 is a screenshot similar to that of FIG. 7, but indicating that a change to the active configuration file has occurred.
Figure 18:
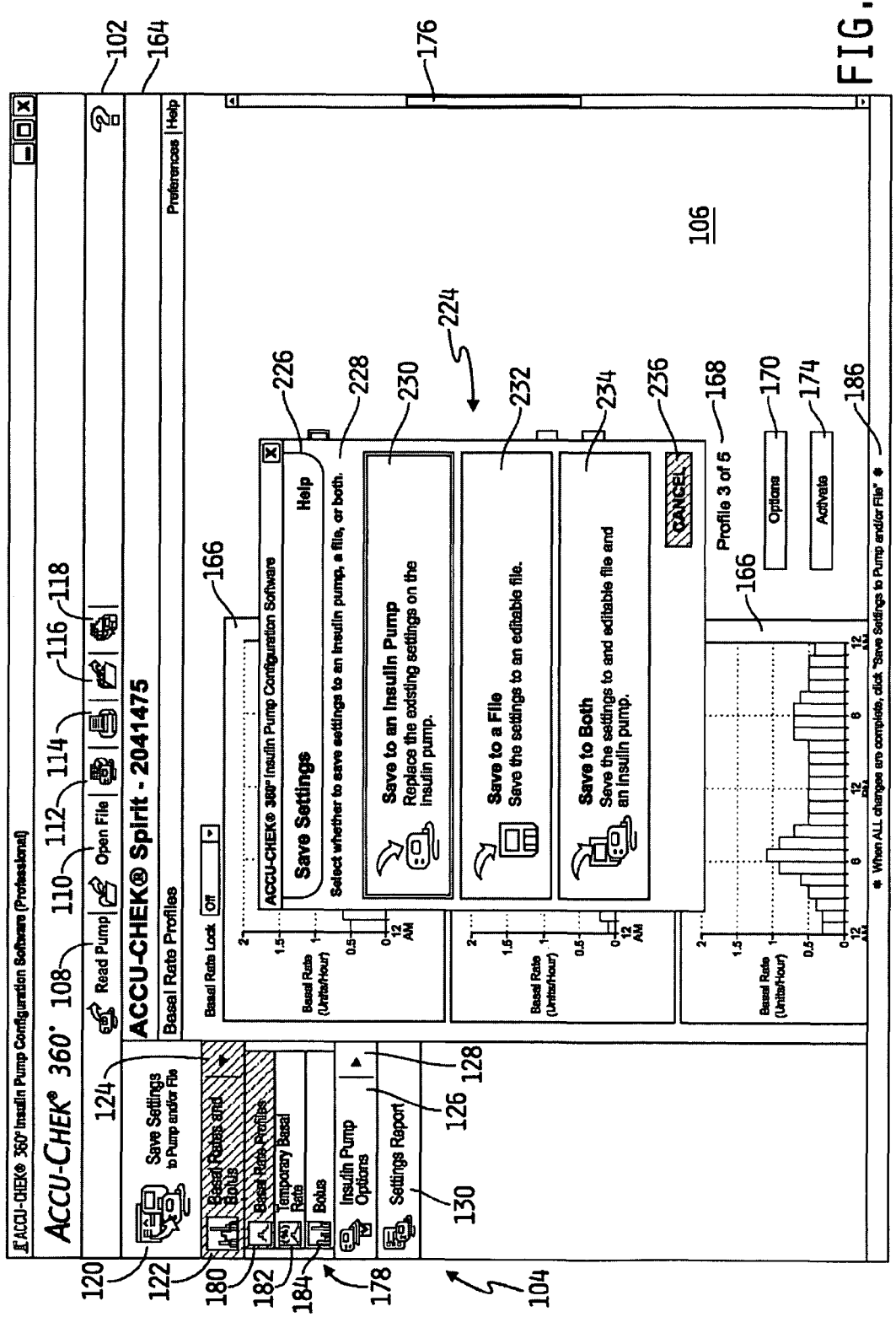
FIG. 18 is a screenshot similar to that of FIG. 12.

When the operator activates OK button 208, FIG. 17 is displayed. FIG. 17 is nearly identical to FIG. 7, which was displayed upon completion of uploading the configuration file from pump 24. Here, however, status bar 186, instead of indicating that the configuration file is unchanged as in FIG. 7, reminds the operator to save the configuration file when the changes are complete. When the operator activates save settings button 120 of navigation menu 104, FIG. 18 is displayed. FIG. 18 is nearly identical to FIG. 12, which was displayed when the operator considered saving the configuration file with invalidity conditions present. As shown in FIG. 18, when no invalidity conditions are present, save to pump button 230 and save to both button 234 are no longer disabled.

Figure 19:
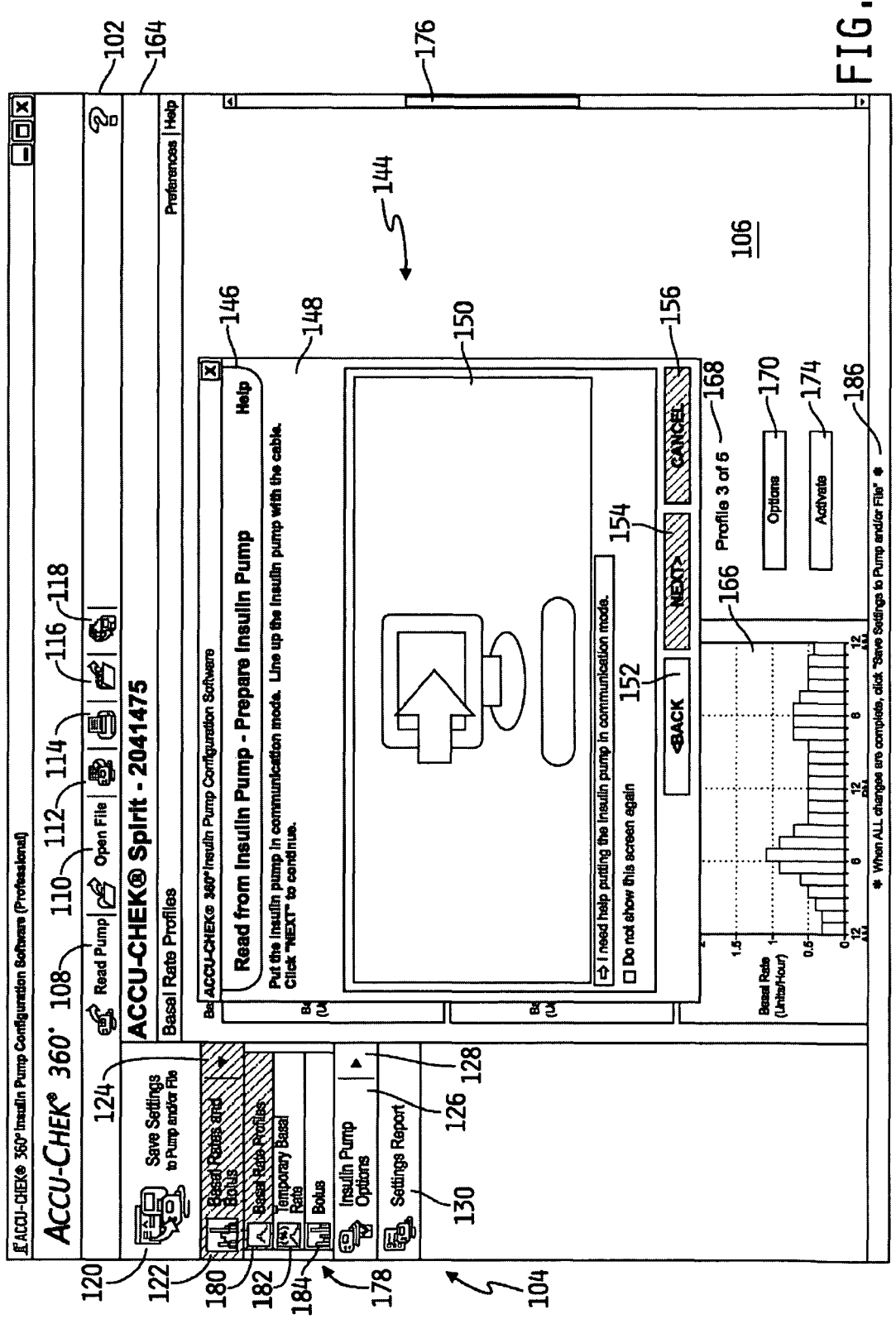
FIGS. 19 and 20 are screenshots similar to those of FIGS. 5 and 6.
Figure 20:
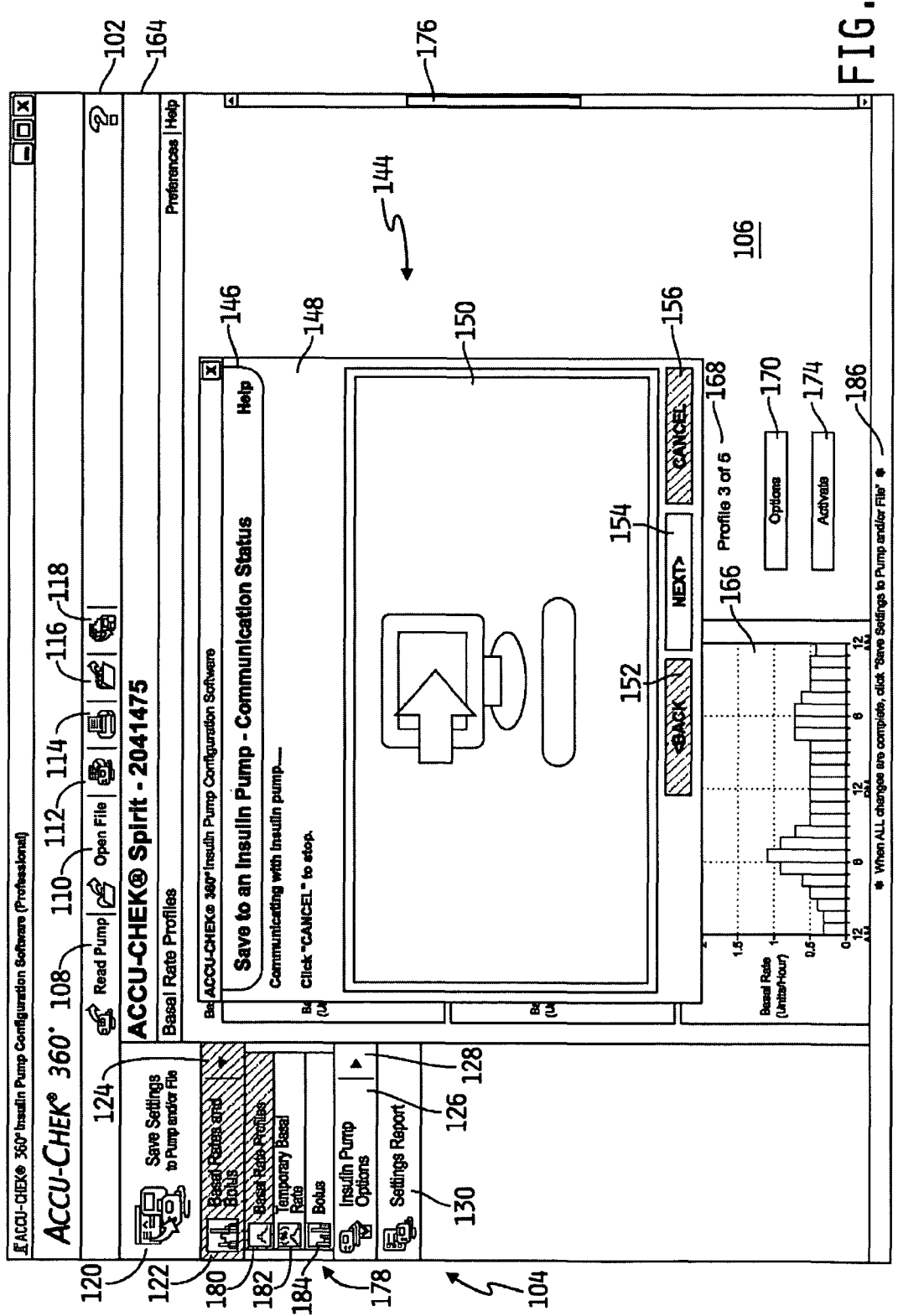

The operator may save the modified configuration file to pump 24 by activating save to pump button 230. FIG. 19 is then displayed with communication status dialog box 144. Title bar 146 indicates that a save to pump operation is being performed. The remainder of dialog box 144 is identical to that depicted in FIG. 5 as part of the read from pump operation. As shown in FIG. 20, after the operator activates next button 154 of dialog box 144, message area 148 indicates that communication with pump 24 is occurring, and instructs the operator to activate cancel button 156 to stop the save operation.

Figure 21:
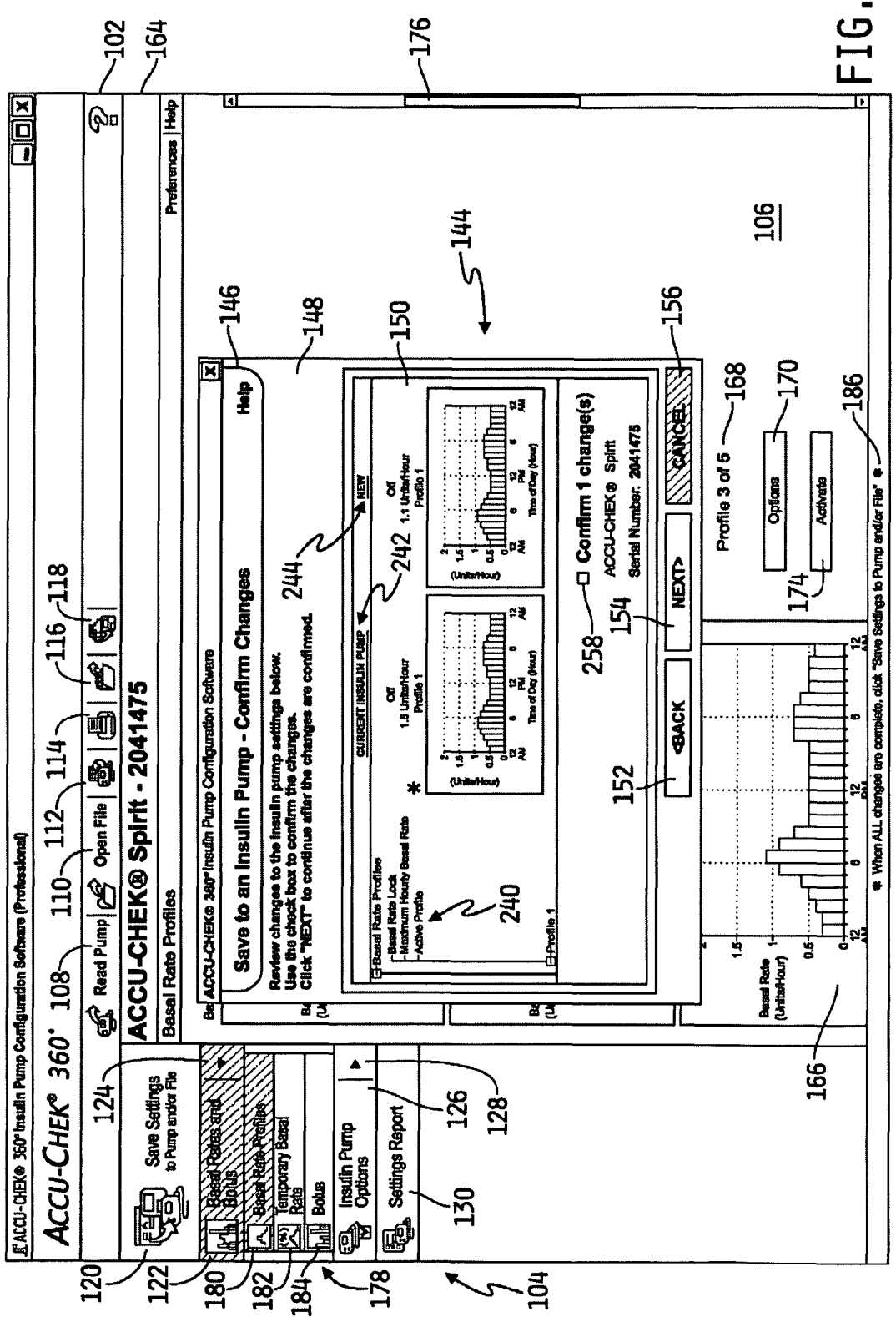
FIGS. 21 and 22 are screenshots similar to those of FIGS. 5 and 6, but including a change confirmation box.
Figure 22:
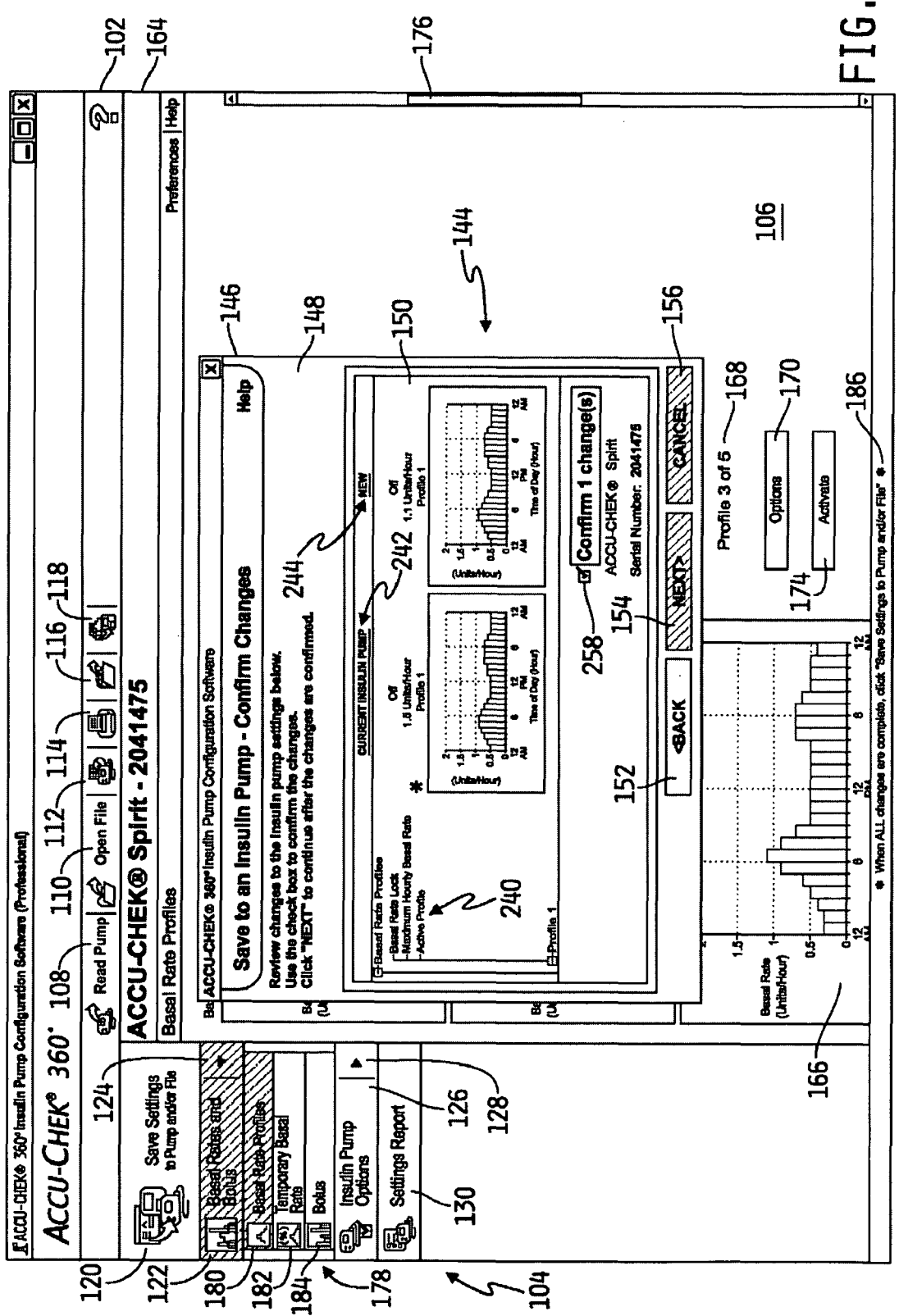
Figure 23:
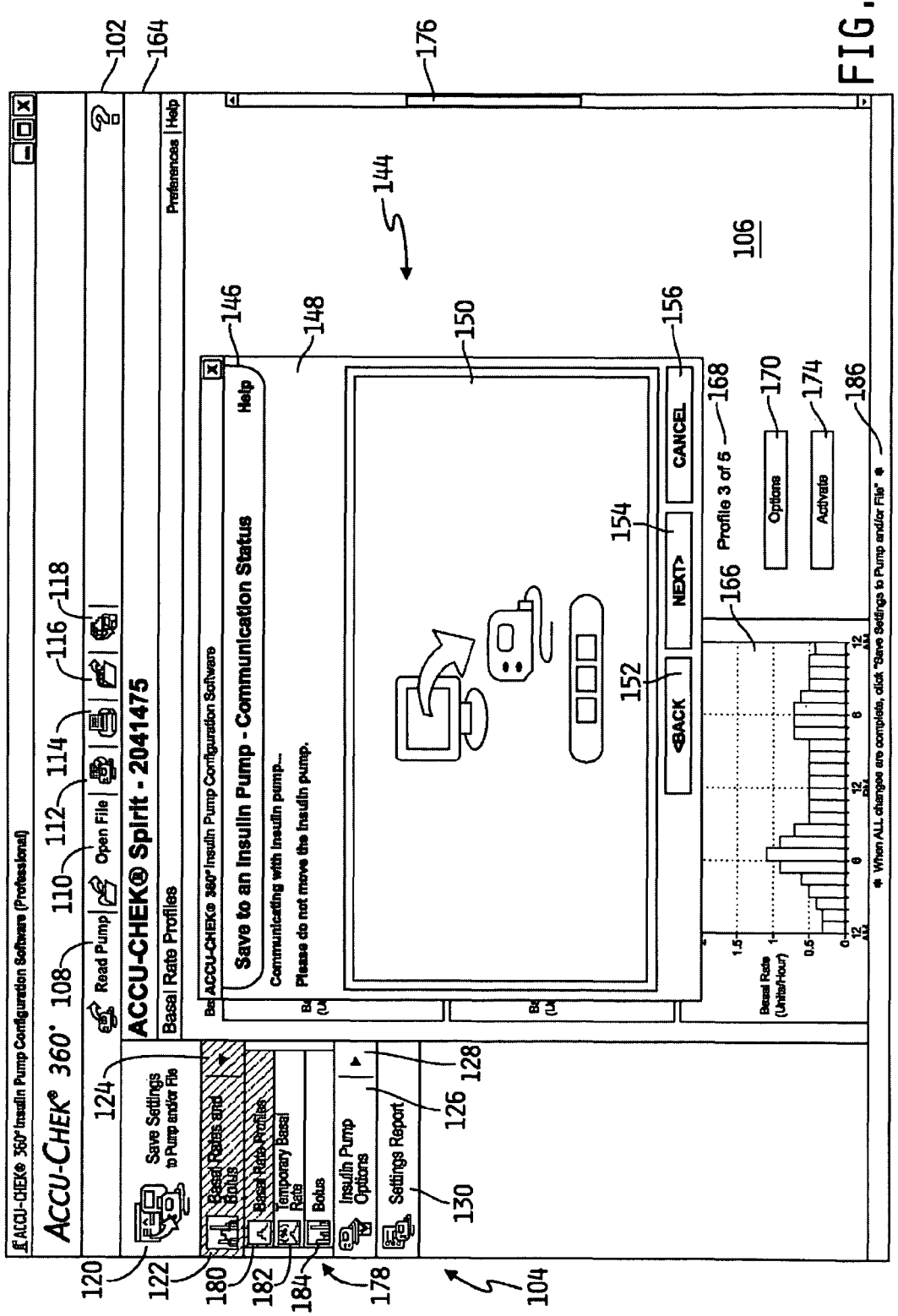
FIGS. 23 and 24 are screenshots similar to those of FIGS. 5 and 6.
Figure 24:
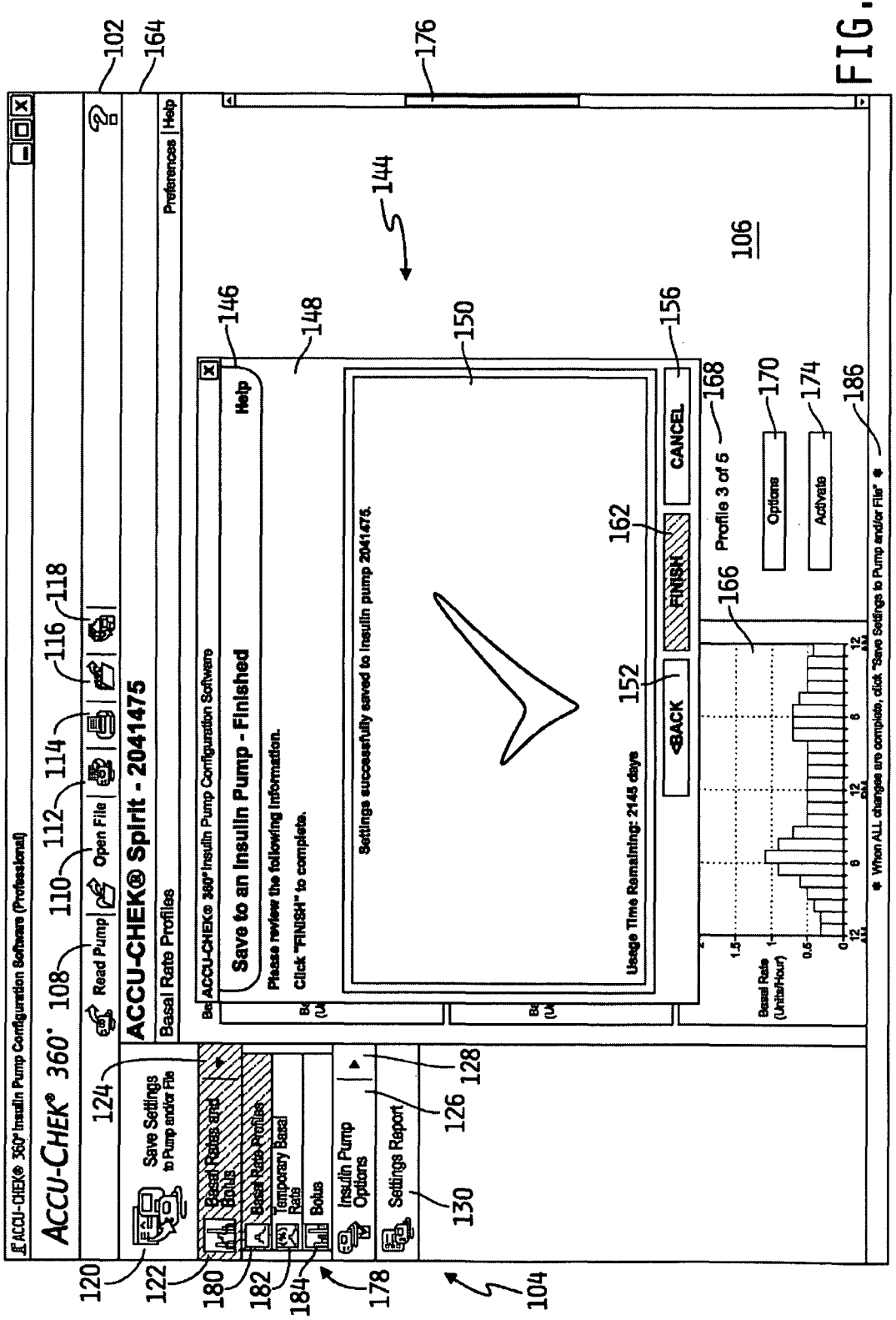
Figure 25:
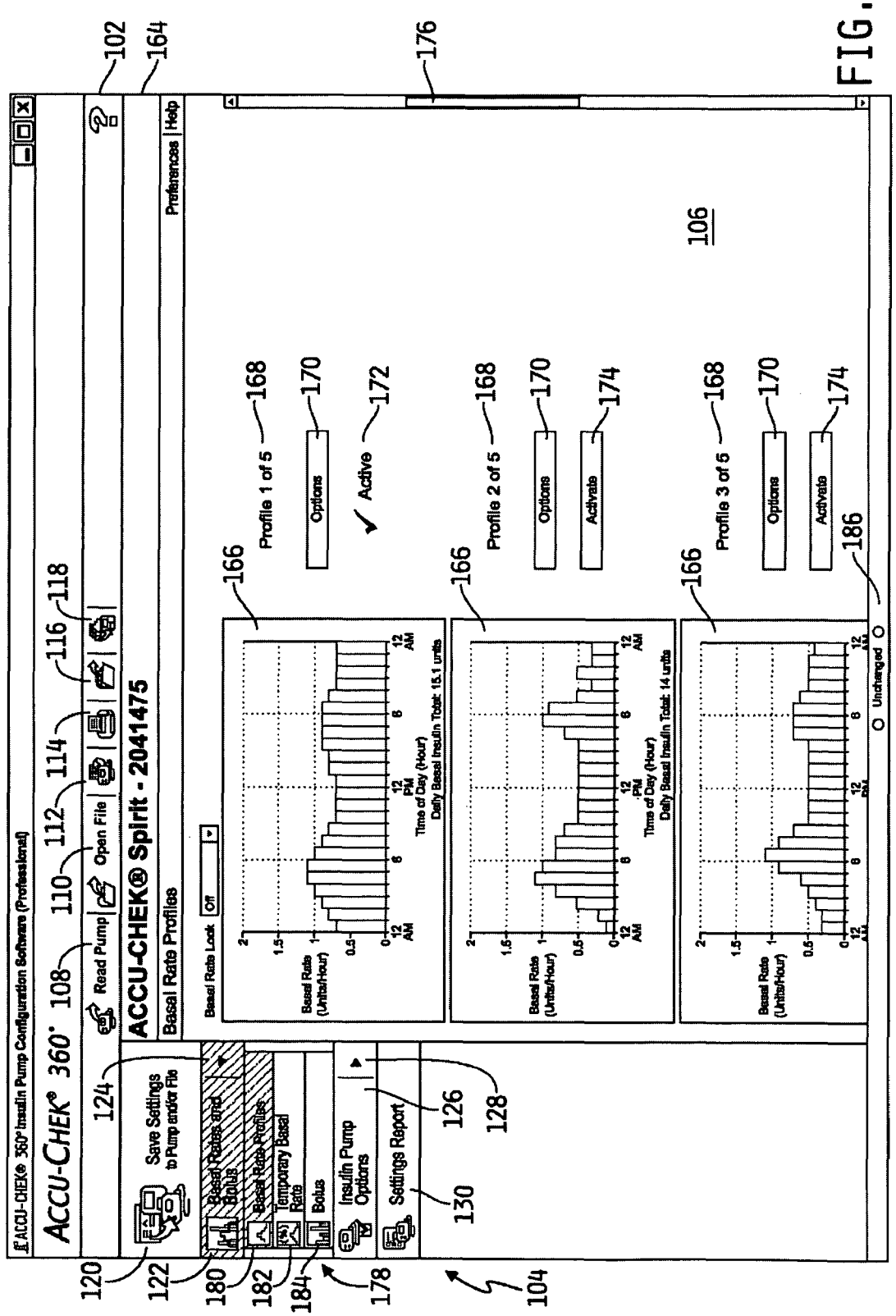
FIG. 25 is a screenshot identical to FIG. 7, but with an underlying parameter change.

Before downloading the modified configuration file to pump 24, software 17 displays confirmation instructions in communications status dialog box 144 as depicted in FIG. 21. As shown, message area 148 includes instructions for reviewing the changes about to be made to the configuration file used by pump 24. Status window 150 includes information similar to that depicted in settings report window 236 of FIG. 13. More specifically, status window 150 includes configuration file tree structure 240, active file information column 242, and modified file information column 244 as described with reference to FIG. 13. As described above, software 17 is configured in this context to automatically scroll through configuration file tree structure 240 and display the changed parameters (or the most important changed parameter if more than one parameter is changed) in the viewable area of status window 150. After the operator reviews the changes to be made to the configuration file by comparing the information in the highlighted data fields 252, 252', the operator must check the confirm changes box 258. As shown in FIG. 22, when confirm changes box 258 is checked, next button 154 is no longer inactive. When the operator activates next button 154, communication status dialog box 144 is generated as depicted in FIG. 23. As shown, message area 148 instructs the operator not to move pump 24, and status window 150 graphically depicts downloading of the modified configuration file. When downloading is complete, dialog box 144 of FIG. 24 is displayed, and the operator activates finish button 162 to complete the save operation. By default, the operator is then presented with FIG. 25, which is identical to FIG. 7. Status bar 186 indicates that the configuration file is unchanged because, after having been saved to pump 24, it reflects the starting point for any further modifications.

While an exemplary embodiment incorporating the principles of the present teachings has been disclosed hereinabove, the present teachings are not limited to the disclosed embodiments. Instead, this application is intended to cover any variations, uses, or adaptations of the disclosed general principles. Further, this application is intended to cover such departures from the present disclosure as come within known or customary practice in the art to which this application pertains and which fall within the limits of the appended claims.

What is claimed is:

1. A method for configuring an insulin pump, including the steps of:
   initiating a workflow for setting parameters of an insulin pump configuration file;
   receiving a setting of a first parameter of a set of parameters;
   receiving a user-selected setting of a second parameter that is dependent upon the setting of the first parameter;

determining whether the setting of the second parameter is invalid based on the setting of the first parameter;

permitting receipt of a user-selected setting of a third parameter while the setting of the second parameter is invalid;

displaying a confirmation screen; and after displaying the confirmation screen, permitting the user to correct the setting of one of the first parameter and the second parameter to cause the setting of the second parameter to be valid.

2. The method of claim 1, wherein the displaying step includes the steps of displaying an icon indicating that the setting of the second parameter is invalid, and providing directions to the user for correcting the invalid setting when a screen pointer is placed over the icon.

3. The method of claim 1, further including the step of displaying an icon indicating that the setting of the second parameter is invalid upon determining that the setting of the second parameter is invalid.

4. The method of claim 1, further including the step of permitting the user to save the configuration file before correcting the setting of the one of the first parameter and the second parameter.

5. The method of claim 4, wherein the configuration file is saved to the insulin pump over a communication link.

6. The method of claim 1, wherein the first parameter relates to a basal rate profile.

7. The method of claim 1, further including the step of responding to a request from the operator to save the configuration file including the invalid setting of the second parameter by preventing the operator from saving the configuration file to the insulin pump.

8. The method of claim 1, wherein the configuration file includes a plurality of basal rate profiles.

9. The method of claim 8, further including the step of prompting the operator to set a parameter associated with one of the basal rate profiles by displaying a thumbnail image of each of the basal rate profiles.

10. A computer readable medium tangibly embodying a program of instructions executable by a computing device to perform method steps including:

prompting an operator to activate a configuration file for controlling the operation of an insulin pump, the configuration file including a first parameter having a first setting and a second parameter having a second setting, the first and second settings being related to one another by a rule;

permitting the operator to change the first and second settings in any order, even when a change causes an invalidity condition based on the rule;

permitting the operator to change a third setting while an invalidity condition exists;

providing visual feedback to the operator when a change in one of the first and second settings causes an invalidity condition;

preventing the operator from saving the activated configuration file to the pump as long as an invalidity condition exists.

11. A system for programming an insulin pump, including:

a computing device having a display and a memory location; and software stored in the memory location for execution by the computing device, the software facilitating a workflow for setting parameters of a configuration file that controls operation of the pump, the workflow including the steps of prompting an operator to activate the configuration file;

displaying a representation of a first parameter on the display;

responding to the operator's selection of the first parameter by enabling the operator to change an original value for the first parameter;

determining that the changed value is invalid because the changed value violates a rule relating the first parameter to a second parameter;

maintaining the changed value in the active configuration file;

displaying an invalid item icon on the display in association with the changed value;

responding to a request from the operator to save the active configuration file including the changed value by preventing the operator from saving the active configuration file to the pump.

12. The system of claim 11, wherein the workflow further includes the step of displaying a settings report to the operator, the settings report including a configuration file tree structure that identifies the first parameter, an active file information column including the original value of the first parameter, and a modified file information column including the changed value of the first parameter.

13. The system of claim 12, wherein the settings report further includes a first invalid item icon associated with the changed value.

14. The system of claim 13, wherein the settings report further includes a second invalid item icon associated with the second parameter.

15. The system of claim 13, wherein the software is configured to automatically position the configuration file tree structure such that the changed value is located in a viewable area of the display.

16. The system of claim 11, wherein the determining step further includes the step of displaying on a status bar an indication that the changed value is invalid.

17. The system of claim 11, wherein the workflow further includes the step of permitting the operator, after the maintaining step, to modify one of the changed value and a value of the second parameter so that the rule is no longer violated.

18. The system of claim 17, wherein the workflow further includes the step of responding to a request from the operator to save the active configuration file when the rule is no longer violated by prompting the operator to select one of the pump and the memory location as a destination for the active configuration file.

19. The system of claim 18, wherein the workflow further includes the step of prompting the operator to confirm the change of the value from the original value to the changed value.

20. The system of claim 19, wherein the prompting the operator to confirm step includes the step of displaying a representation of the original value and the changed value.

* * * * *